United States Patent
Liu et al.

(10) Patent No.: US 7,625,933 B2
(45) Date of Patent: Dec. 1, 2009

(54) INDOLES HAVING ANTI-DIABETIC ACTIVITY

(75) Inventors: Kun Liu, Edison, NJ (US); Peter T. Meinke, Scotch Plains, NJ (US); Harold B. Wood, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 472 days.

(21) Appl. No.: 11/631,465

(22) PCT Filed: Jun. 28, 2005

(86) PCT No.: PCT/US2005/022906

§ 371 (c)(1),
(2), (4) Date: Dec. 29, 2006

(87) PCT Pub. No.: WO2006/014262

PCT Pub. Date: Feb. 9, 2006

(65) Prior Publication Data

US 2008/0119531 A1    May 22, 2008

Related U.S. Application Data

(60) Provisional application No. 60/585,046, filed on Jul. 2, 2004.

(51) Int. Cl.
*A61K 31/422* (2006.01)
*C07D 263/04* (2006.01)
*C07D 413/10* (2006.01)

(52) U.S. Cl. .............. 514/376; 548/215; 548/227; 548/250; 548/253; 514/374; 514/381; 514/382

(58) Field of Classification Search .......... 548/215, 548/227, 250, 253; 514/374, 376, 381, 382
See application file for complete search history.

(56) References Cited

U.S. PATENT DOCUMENTS

| | | | | |
|---|---|---|---|---|
| 7,186,746 | B2 * | 3/2007 | Acton et al. | 514/419 |
| 7,345,085 | B2 * | 3/2008 | Acton et al. | 514/419 |
| 7,393,960 | B2 * | 7/2008 | Acton et al. | 548/241 |

FOREIGN PATENT DOCUMENTS

| | | |
|---|---|---|
| WO | WO 01/30343 | 5/2001 |
| WO | WO 02/08188 | 1/2002 |
| WO | WO 2004/019869 | 3/2004 |
| WO | WO 2004/020408 | 3/2004 |
| WO | WO 2004/020409 | 3/2004 |
| WO | WO 2004/020409 | 11/2004 |

* cited by examiner

*Primary Examiner*—Golam M Shameem
(74) *Attorney, Agent, or Firm*—Richard C. Billups; Catherine D. Fitch

(57) ABSTRACT

Indoles of Formula I having —X-aryl-$(CH_2)_x$-oxazolidinedione and —X-heteroaryl-$(CH_2)_x$-oxazolidinedione substituents on the N atom of the indole ring, where x is 0 or 1, and —X— is a bond or —$CH_2$—, and their thiazolidinedione analogs, are PPAR gamma agonists or partial agonists and are useful in the treatment and control of type II diabetes, including hyperglycemia, dyslipidemia, hyperlipidemia, hypercholesterolemia, hypertriglyceridemia, and obesity that are often associated with type 2 diabetes.

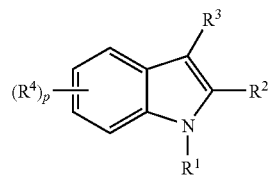

17 Claims, No Drawings

INDOLES HAVING ANTI-DIABETIC ACTIVITY

CROSS REFERENCE TO RELATED APPLICATIONS

This application is a U.S. National Phase application under 35 U.S.C. § 371 of PCT Application No. PCT/US2005/022906, filed Jun. 28, 2005, which claims priority under 35 U.S.C. § 119(e) from U.S. Application No. 60/585,046, filed Jul. 2, 2004.

FIELD OF THE INVENTION

The instant invention is concerned with indoles having a thiazolidine-2,4-dione or oxazolidine-2,4-dione substituent, and pharmaceutically acceptable salts and prodrugs thereof, which are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients are insulin resistant, which means that they have a resistance to the effect of insulin in stimulating glucose and lipid metabolism in the main insulin-sensitive tissues, which are muscle, liver and adipose tissues. Patients who are insulin resistant but not diabetic compensate for the insulin resistance by secreting more insulin, so that serum glucose levels are not elevated enough to meet the criteria of Type 2 diabetes. In patients with Type 2 diabetes, even elevated plasma insulin levels are insufficient to overcome the pronounced insulin resistance.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance or Type 2 diabetes often have several symptoms that together are referred to as syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Insulin resistance is not primarily caused by a diminished number of insulin receptors but by a post-insulin receptor binding defect that is not yet completely understood. This lack of responsiveness to insulin results in insufficient insulin-mediated activation of uptake, oxidation and storage of glucose in muscle and inadequate insulin-mediated repression of lipolysis in adipose tissue and of glucose production and secretion in the liver.

There are several available treatments for type 2 diabetes, each of which has its own limitations and potential risks. Physical exercise and a reduction in dietary intake of calories often dramatically improve the diabetic condition and are the best first line treatment of type 2 diabetes. Compliance with this treatment is very poor because of well-entrenched sedentary lifestyles and excess food consumption, especially of foods containing high amounts of fat. A widely used drug treatment involves the administration of meglitinide or a sulfonylurea (e.g. tolbutamide or glipizide), which are insulin secretagogues. These drugs increase the plasma level of insulin by stimulating the pancreatic β-cells to secrete more insulin. When administration of a sulfonylurea or meglitinide becomes ineffective, the amount of insulin in the body can be supplemented by the injection of insulin so that insulin concentrations are high enough to stimulate even the very insulin-resistant tissues. However, dangerously low levels of plasma glucose can result from administration of insulin and/or insulin secretagogues, and an increased level of insulin resistance due to the even higher plasma insulin levels can occur.

The biguanides are another class of drugs that are widely used to treat type 2 diabetes. The two best known biguanides, phenformin and metformin, cause some correction of hyperglycemia without risk of causing hypoglycemia. The biguanides can be used either with insulin or with an insulin secretagogue without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensitization that is observed with the glitazones. New PPAR agonists are being developed for the treatment of Type 2 diabetes and/or dyslipidemia. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism.

PPAR agonists, and particularly glitazones, have had shortcomings which have so far detracted from their attractiveness. Some of the compounds, especially troglitazone, have exhibited liver toxicity. Troglitazone was eventually withdrawn from the marketplace because of hepatotoxicity. Another weakness in the currently marketed PPAR agonists is that monotherapy for type 2 diabetes produces only modest efficacy—a reduction in average plasma glucose of ≈20% and a decline from ≈9.0% to ≈8.0% in HemoglobinA1C. The current compounds also do not greatly improve lipid metabolism, and may actually have a negative effect on the lipid profile. These shortcomings have provided an incentive to develop better insulin sensitizers for Type 2 diabetes which function via similar mechanism(s) of action.

Recently, there have been reports of compounds that are PPAR gamma antagonists or partial agonists. WO01/30343 describes a specific compound that is a PPAR partial agonist/antagonist that is useful for the treatment of obesity and Type 2 diabetes. WO02/08188, WO2004/020408, WO2004/020409, and WO2004/019869 disclose classes of PPAR agonists and partial agonists that are indole derivatives and that are useful in the treatment of Type 2 diabetes, with reduced side effects relating to body and heart weight gain.

SUMMARY OF THE INVENTION

The class of compounds described herein is a new class of PPAR-gamma agonists and partial agonists. The compounds are potent ligands of the PPAR gamma nuclear receptor. The class of compounds includes many compounds that are PPARγ partial agonists, but also may include PPARγ full agonists and/or PPARγ antagonists. Some compounds may also have PPARα activity in addition to PPARγ activity. The compounds are useful in the treatment and control of hyperglycemia and insulin resistance. The compounds are expected to be efficacious in the treatment of non-insulin dependent diabetes mellitus (NIDDM) in human and other mammalian patients, particularly in the treatment of hyperglycemia, and in the treatment of conditions associated with NIDDM, including hyperlipidemia, dyslipidemia, obesity, hypercholesterolemia, hypertriglyceridemia, atherosclerosis, vascular restenosis, inflammatory conditions, and other PPAR mediated diseases, disorders and conditions.

The compounds may also be useful in the treatment of one or more lipid disorders, including mixed or diabetic dyslipidemia, isolated hypercholesterolemia, which may be manifested by elevations in LDL-C and/or non-HDL-C, hyperapoBliproteinemia, hypertriglyceridemia, an increase in triglyceride-rich-lipoproteins, and low HDL cholesterol concentrations. They may also be useful in the treatment or amelioration of atherosclerosis, obesity, vascular restenosis, inflammatory conditions, psoriasis, polycystic ovary syndrome, and other PPAR mediated diseases, disorders and conditions.

The present invention is directed to compounds having Formula I

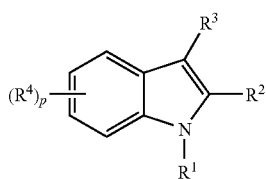

I and pharmaceutically acceptable salts and prodrugs thereof. In the compounds having Formula I:

$R^1$ is selected from
(a) —X-Aryl-Y-Z, and
(b) —X-Heteroaryl-Y-Z, where Aryl and Heteroaryl are optionally substituted with 1-3 groups independently selected from A, wherein the substituent groups A can be on any available position of Heteroaryl (i.e. carbon or nitrogen) when $R^1$ is —X-Heteroaryl-Y-Z;

Aryl is phenyl or naphthyl;

Heteroaryl is a monocyclic or fused bicyclic aromatic ring containing 1-4 heteroatoms independently selected from N, O and S, including —S(O)— and —S(O)$_2$—, wherein each ring contains 5 to 6 atoms;

X and Y are independently selected from the group consisting of a bond and —CR$^5$R$^6$—;

Z is

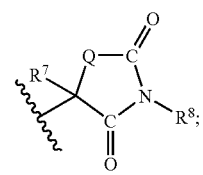

Q is selected from the group consisting of S and O;

A is selected from $C_1$-$C_4$ alkyl, $C_2$-$C_4$ alkenyl, —O$C_1$-$C_4$ alkyl, and halogen, wherein alkyl, alkenyl, and —Oalkyl are each optionally substituted with 1-5 halogens;

$R^2$ is $C_1$-$C_4$ alkyl, which is optionally substituted with 1-5 halogens;

$R^3$ is selected from
(a) Benzisoxazolyl,
(b) Aryl,
(c) —C(=O)Aryl,
(d) —OAryl, and
(e) —S(O)$_n$Aryl, where $R^3$ is optionally substituted with 1-3 substituent groups independently selected from halogen, $C_1$-$C_3$ alkyl, and —O$C_1$-$C_3$ alkyl, wherein $C_1$-$C_3$ alkyl and —O$C_1$-$C_3$ alkyl are optionally substituted with 1-5 halogens;

$R^4$, $R^5$, and $R^6$ are each independently selected from hydrogen, halogen, $C_1$-$C_3$ alkyl, and —O$C_1$-$C_3$ alkyl, wherein $C_1$-$C_3$ alkyl and —O$C_1$-$C_3$ alkyl are optionally substituted with 1-5 halogens;

$R^7$ is selected from H, $C_1$-$C_3$ alkyl, and halogen, wherein $C_1$-$C_3$ alkyl is optionally substituted with 1-3 F;

$R^8$ is selected from the group consisting of H and CH$_3$;

n is an integer from 0 to 2; and p is an integer from 0 to 3.

In the above definitions and subsequent definitions, alkyl groups may be either linear or branched, unless otherwise specified.

DETAILED DESCRIPTION OF THE INVENTION

The invention has numerous embodiments. It provides compounds of Formula I, including pharmaceutically acceptable salts of these compounds, prodrugs of these compounds, and pharmaceutical compositions comprising these compounds and a pharmaceutically acceptable carrier.

In preferred embodiments of the compounds of Formula I, $R^8$ is H.

In many preferred embodiments, $R^1$ is —X-phenyl-YZ.

In many preferred embodiments, X and Y are each independently a bond or —$CH_2$—.

In many preferred embodiments of the invention, A is selected from the group consisting of halogen, —$CF_3$, —$OCF_3$, —$CH_3$, and —$OCH_3$.

In many preferred embodiments, $R^2$ is $C_{1-3}$ alkyl or —$CF_3$.

In many preferred embodiments, $R^2$ is —$CH_3$.

In many preferred compounds, $R^4$ is selected from the group consisting of —$OCH_3$, —$OCF_3$, —$CH_3$ and —$CF_3$; and p is 1.

In many preferred compounds, $R^3$ is selected from the group consisting of:

(a) 3-Benzisoxazolyl,
(b) Phenyl,
(c) —C(=O)Phenyl, and
(d) —OPhenyl, wherein $R^3$ is optionally substituted with 1-2 groups independently selected from halogen, —$OCH_3$, —$OCF_3$, $CH_3$, and $CF_3$.

In preferred subsets of compounds described above, $R^1$ is —X-phenyl-YZ or —X-tetrazolyl-YZ, where phenyl is optionally substituted with 1-2 groups independently selected from A; A preferred subgroup comprises compounds in which $R^1$ is —X-phenyl-YZ, where phenyl is optionally substituted with 1-2 groups independently selected from A;

X and Y are independently selected from a bond and —$CH_2$—;

A is selected from the group consisting of F, Cl, I, —$CF_3$, —$OCF_3$, —$CH_3$, and —$OCH_3$;

$R^2$ is —$CH_3$;

$R^4$ is selected from the group consisting of Cl, —$CF_3$, —$OCF_3$, —$CH_3$, and —$OCH_3$;

$R^7$ is selected from the group consisting of H, $CH_3$, and $CF_3$;

$R^8$ is H; and p is 0 or 1, and is more preferably 1.

In many preferred embodiments of the compounds described above, Q is O, and X and Y are —$CH_2$—.

In many other preferred embodiments, Q is O, X is —$CH_2$—, and Y is a bond.

In many of the compounds described above Heteroaryl is pyridyl, quinolyl, furyl, tetrazolyl, isoxazolyl, oxazolyl, azoxazolyl, pyrazolyl, or thiazolyl. Compounds in which Heteroaryl is tetrazolyl have desirable properties.

Structures of specific compounds are provided in Tables 1 and 2. The syntheses of the specific compounds in Table 1 are provided hereinafter in the Examples. The compounds in Table 2 were made by generally following the methods disclosed herein, and can readily be made by a practitioner of synthetic chemistry. Mass spectral data for the compounds in Table 2 are also provided in Table 2A, which follows Table 2.

TABLE 1

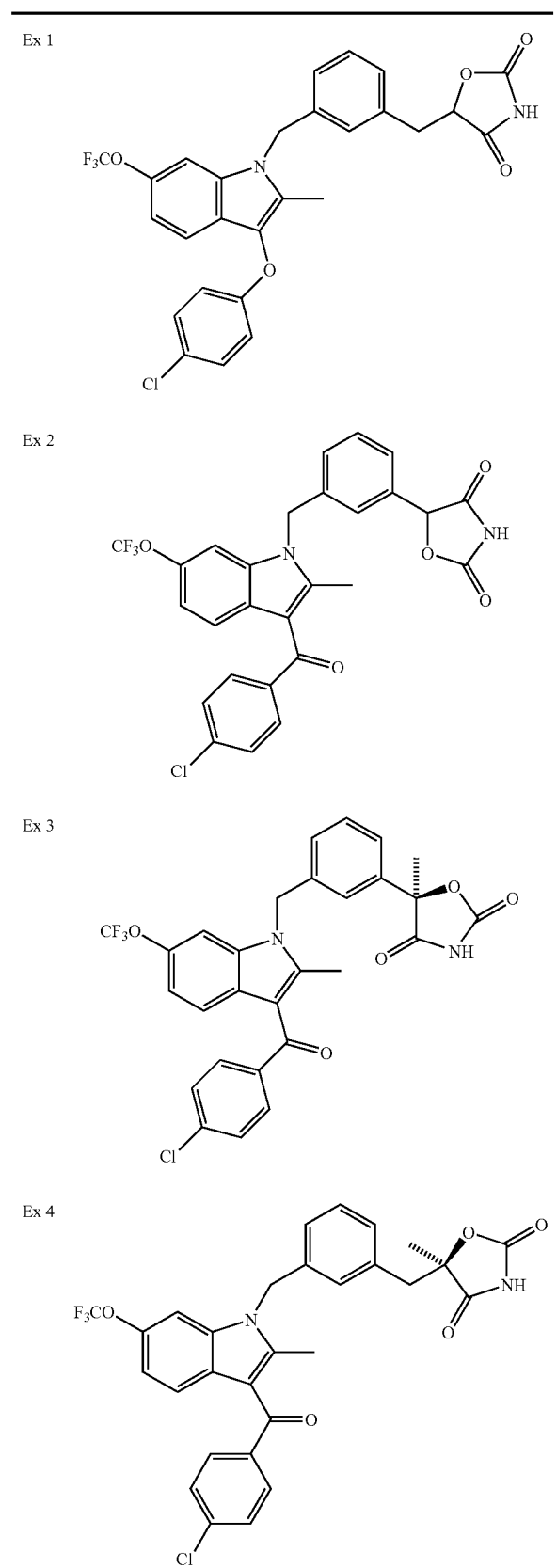

Ex 1

Ex 2

Ex 3

Ex 4

TABLE 1-continued
Ex 5
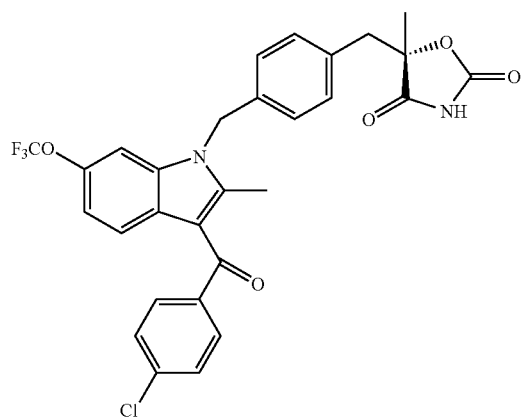
and
Ex 6
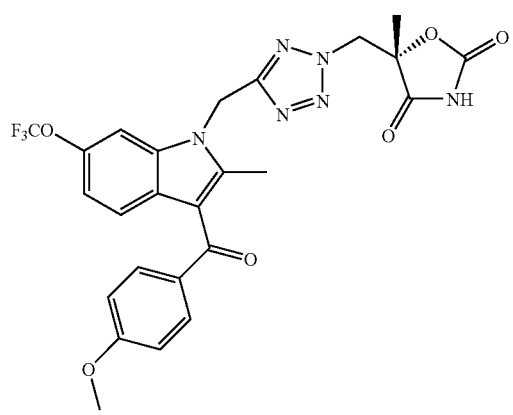
TABLE 2
Other Compounds
2.1  Chiral
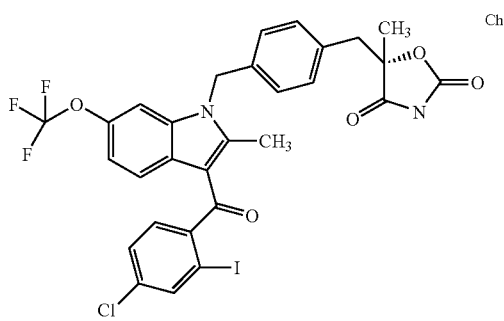
TABLE 2-continued
Other Compounds
2.2  Chiral
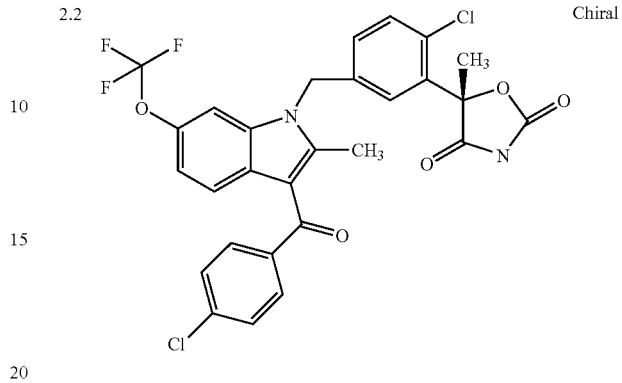
2.3  Chiral
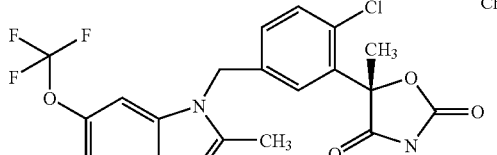
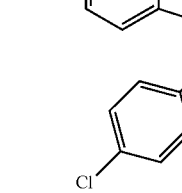
2.4
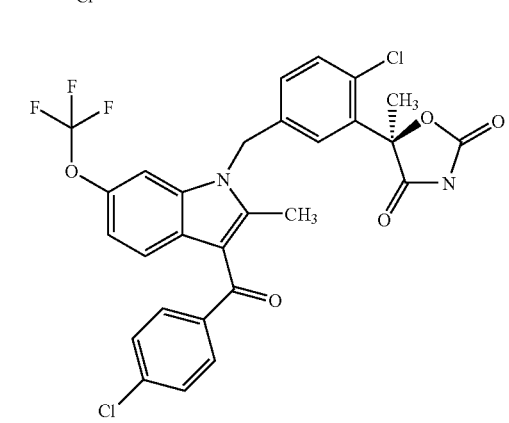
2.5
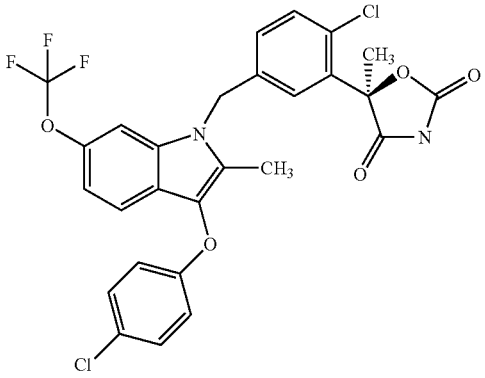

TABLE 2-continued
Other Compounds
2.6 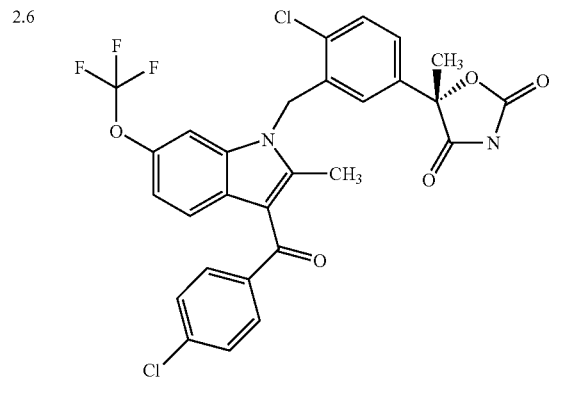
2.7 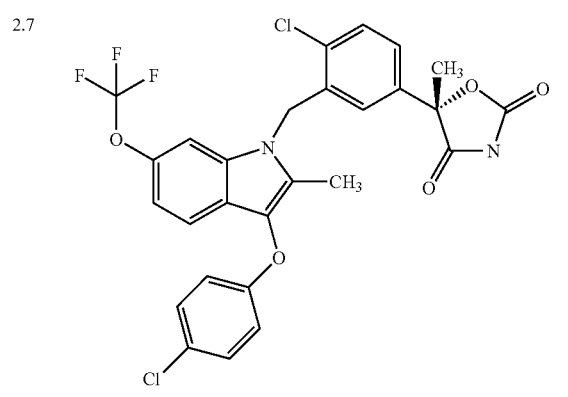
2.8 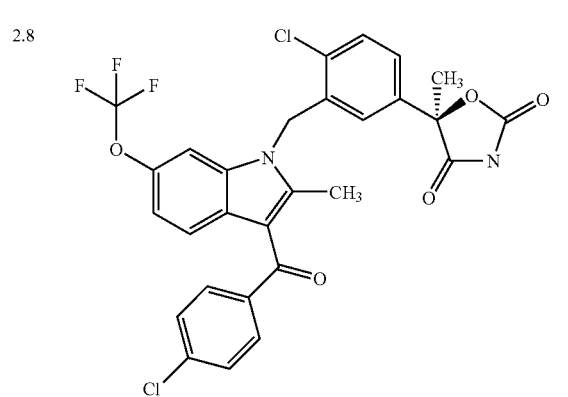
2.9 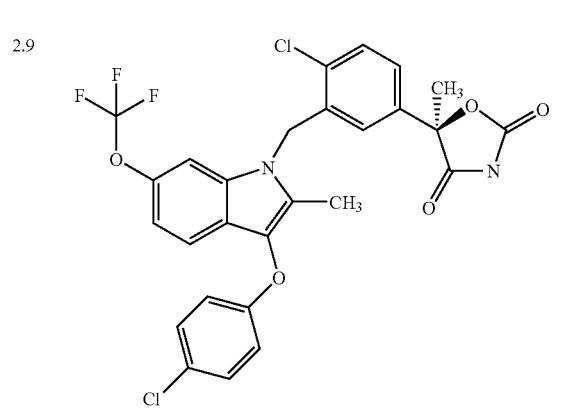
TABLE 2-continued
Other Compounds
2.10 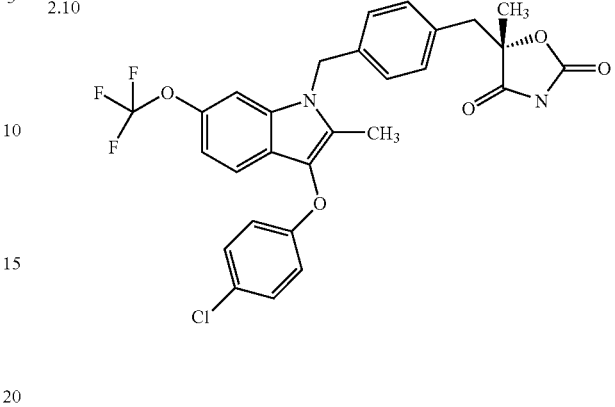
2.11 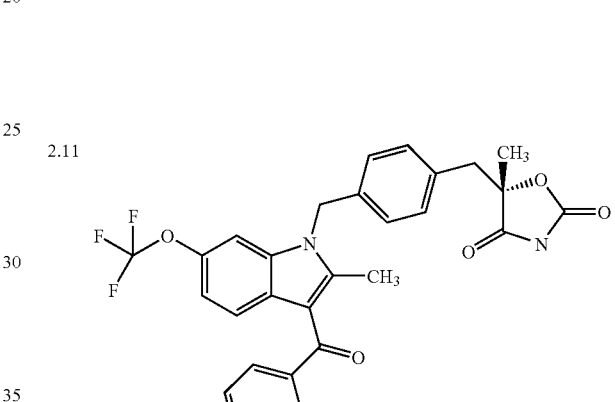
2.12 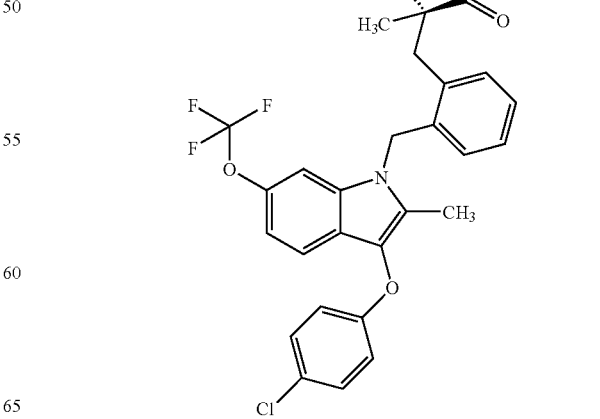

TABLE 2-continued
Other Compounds
2.13 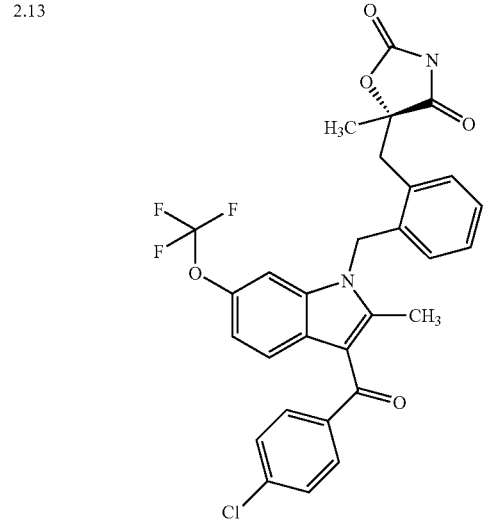
2.14 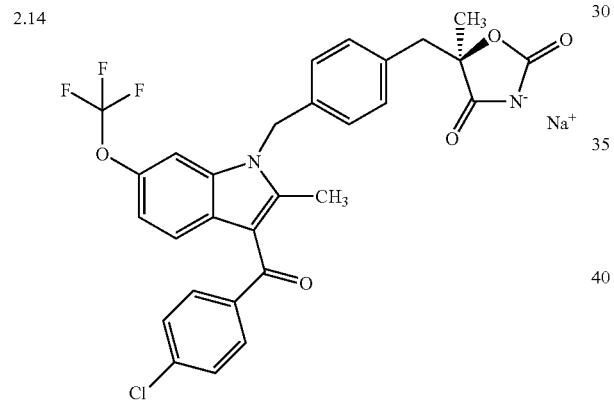
2.15 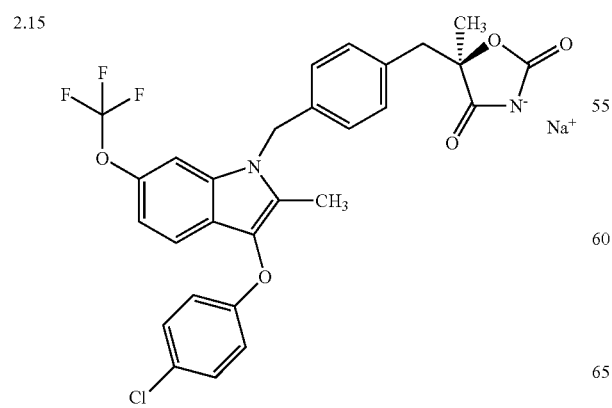
TABLE 2-continued
Other Compounds
2.16 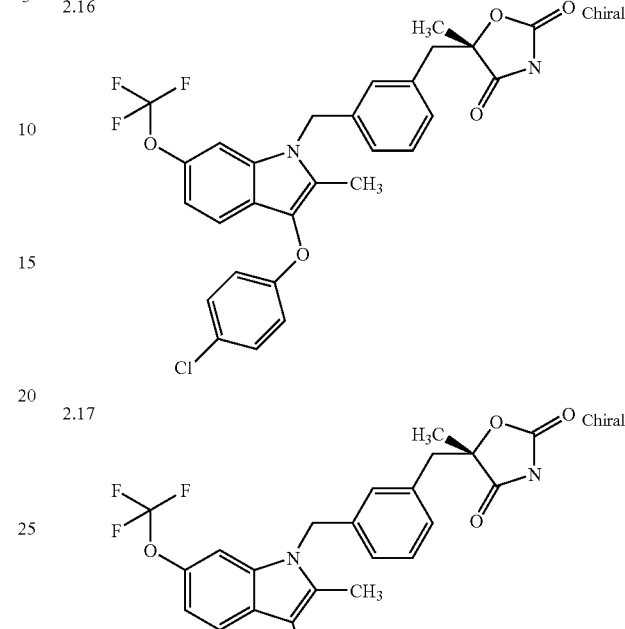
2.17 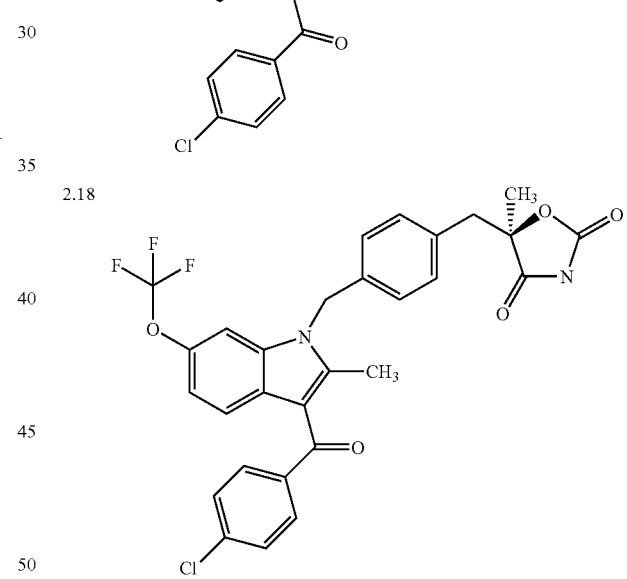
2.18 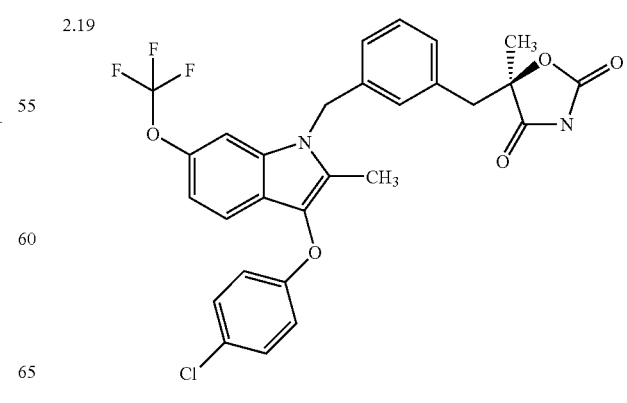
2.19

TABLE 2-continued
Other Compounds
2.20 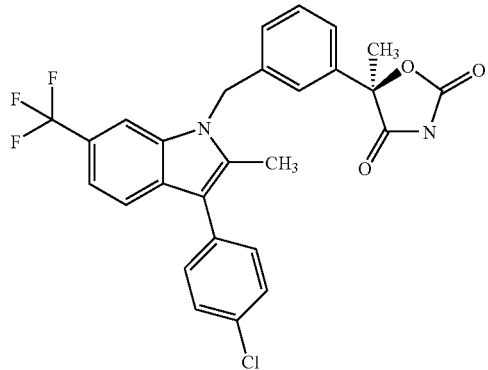
2.21 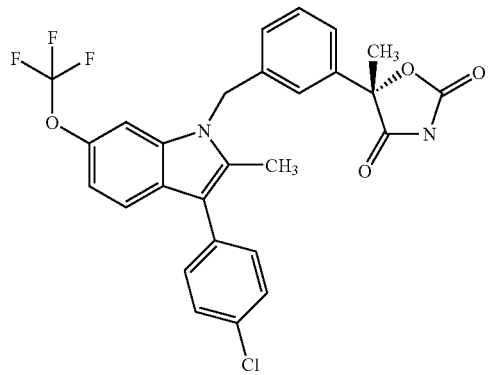
2.22 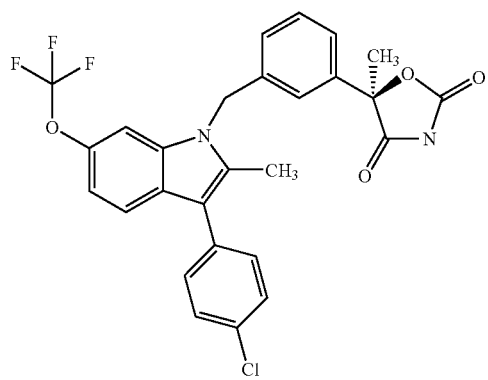
2.23 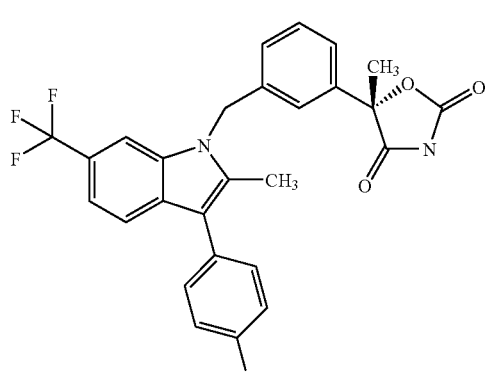
TABLE 2-continued
Other Compounds
2.24 Chiral 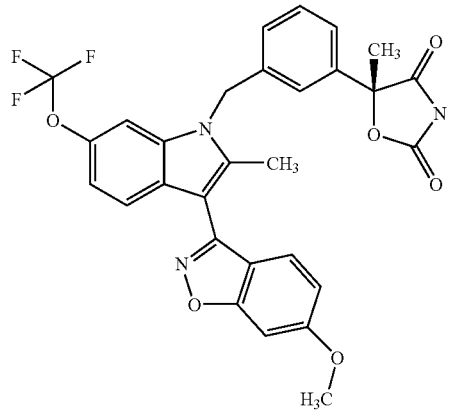
2.25 Chiral
2.26
2.27 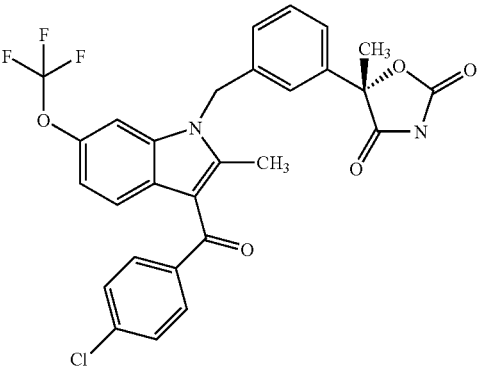

TABLE 2-continued

Other Compounds 2.28 Chiral
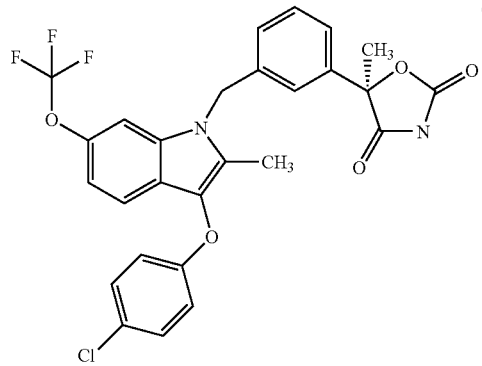

2.29
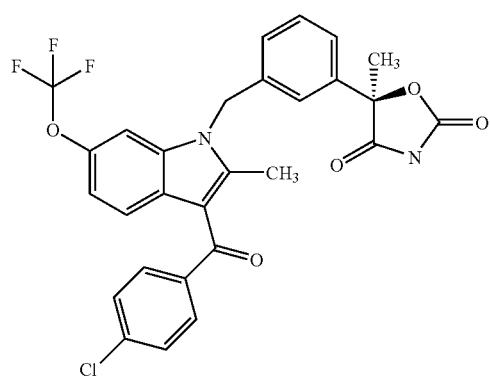

2.30
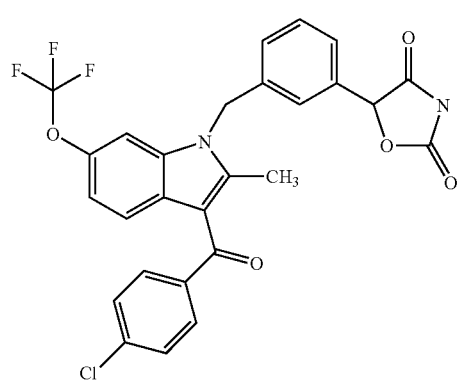

2.31
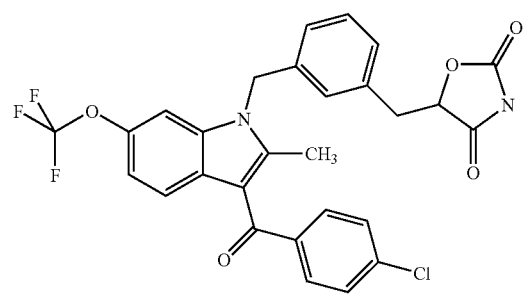

TABLE 2-continued

Other Compounds 2.32

[structure]

TABLE 2A

| Examples | LC-MS | Retention Time | HPLC Method |
|---|---|---|---|
| 2.1 | m/z 697 | 3.82 min | A (see Examples) |
| 2.2 | 591 (M + 1) | 3.75 min | A |
| 2.3 | 579 (M + 1) | 4.06 min | A |
| 2.4 | 591 (M + 1) | 3.76 min | A |
| 2.5 | 579 (M + 1) | 4.07 min | A |
| 2.6 | 591 (M + 1) | 3.91 min | A |
| 2.7 | 579 (M + 1) | 4.24 min | A |
| 2.8 | 591 (M + 1) | 3.95 min | A |
| 2.9 | 579 (M + 1) | 4.23 min | A |
| 2.10 | m/z 559, 432 | 4.08 min | A |
| 2.11 | m/z 571 | 3.76 min | A |
| 2.12 | m/z 559, 432 | 4.14 min | A |
| 2.13 | m/z 571 | 3.82 min | A |
| 2.14 | 571 (M + 1) | 3.67 min | A |
| 2.15 | 559 (M + 1) | 3.96 min | A |
| 2.16 | m/z 559, 432 | 3.95 min | A |
| 2.17 | m/z 571 | 3.67 min | A |
| 2.18 | 571 (M + 1) | 3.66 min | A |
| 2.19 | 559 (M + 1) | 3.95 min | A |
| 2.20 | 513 (M + 1) | 4.26 min | A |
| 2.21 | 529 (M + 1) | 4.42 min | A |
| 2.22 | 529 (M + 1) | 4.42 min | A |
| 2.23 | 513 (M + 1) | 4.27 min | A |
| 2.24 | 566 (M + 1) | 3.93 min | A |
| 2.25 | 566 (M + 1) | 4.07 min | A |
| 2.26 | 545 (M + 1) | 4.19 min | A |
| 2.27 | 557 (M + 1) | 3.97 min | A |
| 2.28 | 545 (M + 1) | 4.18 min | A |
| 2.29 | 557 (M + 1) | 3.98 min | A |
| 2.30 | 543 (M + 1) | 3.65 min | A |
| 2.31 | 557 (M + 1) | 4.00 min | A |
| 2.32 | 545 (M + 1) | 4.26 min | A |

The compounds of this invention can be used in pharmaceutical compositions comprising the compound or a pharmaceutically acceptable salt thereof and a pharmaceutically acceptable carrier. The compounds of this invention can be used in pharmaceutical compositions in which a compound of Formula I or a pharmaceutically acceptable salt thereof is the only active ingredient, or in compositions that also include additional active ingredients.

The compounds of the invention and pharmaceutically acceptable salts thereof can be used in the manufacture of medicaments for the treatment of type 2 diabetes mellitus in a human or other mammalian patient, and in the manufacture of medicaments for other diseases described herein that are treated by the compounds.

The compounds as defined above may be used in any of the following methods to treat or control diseases, as well as methods to treat other diseases not listed below, in a mammalian patient, especially a human, by administering to the patient a therapeutically effective amount of a compound of Formula I:

(1) non-insulin dependent diabetes mellitus (type 2 diabetes);
(2) hyperglycemia;
(3) metabolic syndrome;
(4) obesity;
(5) hypercholesterolemia;
(6) hypertriglyceridemia; and/or
(7) one or more lipid disorders, including mixed or diabetic dyslipidemia, low HDL cholesterol, high LDL cholesterol, hyperlipidemia, hypercholesterolemia, and hypertriglyceridemia.

The compounds may also be used in a method for reducing the risks of adverse sequelae associated with metabolic syndrome in a human or other mammalian patient in need of such treatment which comprises administering to the patient a therapeutically effective amount of a compound of Formula I.

The compounds may also be used in a method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

The compounds are especially useful in the treatment of the following diseases, by administering a therapeutically effective amount to a patient in need of treatment:

(1) type 2 diabetes, and especially hyperglycemia resulting from type 2 diabetes;
(2) metabolic syndrome;
(3) obesity; and
(4) hypercholesterolemia.

Definitions

"Ac" is acetyl, which is $CH_3C(O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated or partially unsaturated carbocyclic rings, each having from 3 to 10 carbon atoms, unless otherwise stated. The term also includes a monocyclic ring fused to an aryl group. Examples of cycloalkyl include cyclopropyl, cyclopentyl, cyclohexyl, cycloheptyl, and the like.

A cycloalkylidene group is a divalent cycloalkane radical in which both attachments are at the same carbon. For example, the cyclopropyl group of 1,1-dimethylcyclopropane is a cyclopropylidene group.

"Aryl" (and "arylene") when used to describe a substituent or group in a structure means a monocyclic or bicyclic compound in which all the rings are aromatic and which contains only carbon ring atoms. The term "aryl" can also refer to an aryl group that is fused to a cycloalkyl or heterocycle. "Heterocyclyl," "heterocycle," and "heterocyclic" means a fully or partially saturated monocyclic or bicyclic ring system containing 1-4 heteroatoms independently selected from N, S and O, each of said rings having from 3 to 8 atoms. Examples of aryl substituents include phenyl and naphthyl. Aryl rings fused to cycloalkyls are found in indanyl, indenyl, and tetrahydronaphthyl. Examples of aryl fused to heterocyclic groups are found in 2,3-dihydrobenzofuranyl, dihydrobenzopyranyl, and the like. Examples of heterocycles include tetrahydrofuran, piperazine, and morpholine. Preferred aryl groups are phenyl or naphthyl. Phenyl is generally the most preferred.

"Heteroaryl" (and heteroarylene) means a mono- or fused bicyclic aromatic ring system containing 1-4 heteroatoms selected from N, O and S, including —S(O)— and —S(O)$_2$—, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, azoxazolyl, imidazolyl, triazolyl, tetrazolyl, furyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, and the like. Preferred heteroaryl groups include pyridyl, quinolyl, furyl, tetrazolyl, isoxazolyl, oxazolyl, azoxazolyl, pyrazolyl, and thiazolyl.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites of other compounds, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the present invention are potent ligands having agonist, partial agonist or antagonist activity on one or more of the various peroxisome proliferator activated receptor subtypes, particularly PPARγ. The compounds may also be ligands or agonists, partial agonists or antagonists of the PPARα subtype as well as the PPARγ subtype, resulting in mixed PPARα/γ agonism or in agonism of mainly the PPARα subtype. Some compounds (generally less preferred) may also be PPARδ ligands and have PPARδ activity in addition to their other PPAR activity. The compounds of this invention are useful in treating or controlling diseases, disorders or conditions which are mediated by one or more ligands of the individual PPAR subtypes (eg. γ or α) or a combination of PPAR subtypes (e.g. α/γ). One aspect of the present invention provides a method for the treatment and control of diseases that can be mediated by administration of a PPAR agonist or partial agonist, particularly a PPAR γ agonist or partial agonist, such as type 2 diabetes, by administering to a patient in need of treatment a therapeutically effective amount of a compound of Formula I. Compounds of the present invention may be useful in treating or controlling many PPAR mediated diseases and conditions, including, but not limited to, (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) psoriasis, (23) metabolic syndrome, (24) ovarian hyperandrogenism (polycystic ovarian syndrome), and other disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers, angiogenesis, and Alzheimer's disease.

The present compounds can be used to lower glucose, lipids, and insulin in non-diabetic patients that have impaired glucose tolerance and/or are in a pre-diabetic condition.

The present compounds can be used to treat obesity in a patient in need of such treatment by administering to the patient a therapeutically effective amount of a compound of Formula 1.

The present compounds can be used to treat or reduce the risk of developing atherosclerosis in a patient in need of such treatment by administering to the patient a therapeutically effective amount of a compound of Formula 1.

The present compounds can be used to treat or reduce hyperglycemia in a patient in need of such treatment by administering to the patient a therapeutically effective amount of a compound of Formula 1.

The compounds may have utility in treating osteoporosis. The compounds of this invention may treat osteoporosis or reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors, niacin, niacin receptor agonists, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.01 milligram to about 100 milligrams per kilogram of animal body weight, preferably given as a single daily dose or in divided doses two to six times a day, or in sustained release form. For most large mammals, including humans (e.g. a 70 kg adult), the total daily dosage is from about 0.1 milligrams to about 1000 milligrams, is likely to be from about 0.5 milligrams to about 350 milligrams, and is often from about 1 milligram to about 50 milligrams. For a particularly potent compound, the dosage for an adult human may be as low as 0.1 mg. Examples of daily dosages for a 70 kg adult human are 0.1 mg, 0.5 mg, 1 mg, 2 mg, 5 mg, 10 mg, 25 mg, 50 mg, 100 mg, 150 mg, 200 mg, 250 mg, 350 mg, and 500 mg per day. The daily dosage regimen may be adjusted within the above ranges or even outside of these ranges to provide the optimal therapeutic response.

Oral administration will usually be carried out using tablets. Examples of doses in tablets which may be administered once a day or more than once a day (e.g. 2×, 3×, or (rarely) 4 or more times per day, are 0.1 mg, 0.5 mg, 1 mg, 2 mg, 5 mg, 10 mg, 25 mg, 50 mg, 100 mg, 150 mg, 200 mg, 250 mg, 350 mg, and 500 mg. Other oral forms (e.g. capsules or suspensions) can also be administered in doses having similar sizes.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts of pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy. In general, compositions suitable for oral administration are preferred.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure such as T-131;

(b) biguanides such as metformin and phenformin;

(c) protein tyrosine phosphatase-1B (PTP-1B) inhibitors, (d) dipeptidyl peptidase IV (DP-IV) inhibitors, such as LAF-237, MK-0431, and N,N-7201;

(e) insulin or insulin mimetics;

(f) sulfonylureas such as tolbutamide and glipizide, or related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) niacin receptor agonists, (v) PPARα agonists such as fenofibric acid derivatives (gemfibrozil, clofibrate, fenofibrate and bezafibrate), (vi) cholesterol absorption inhibitors, such as for example ezetimibe, (vii) acyl CoA:cholesterol acyltransferase (ACAT) inhibitors, such as avasimibe, (viii) CETP inhibitors, such as torcetrapib, and (ix) phenolic anti-oxidants, such as probucol;

(i) PPARα/γ dual agonists, such as KRP-297, muraglitazar, tesaglitazar, naveglitazar (LY-818), TAK-559, LY-929, and the like;

(j) PPARδ agonists such as GW501516 and compounds disclosed in WO97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $\beta_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, and (q) GLP-1 analogs, such as exenatide and exendins.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Compounds of the present invention (i.e. compounds having Formula I) can be used to treat one or more diseases or conditions selected from hypercholesterolemia, atherosclerosis, low HDL levels, high LDL levels, hyperlipidemia, hypertriglyceridemia, and dyslipidemia by administering a therapeutically effective amount of a compound of claim 1 in combination with an HMG-CoA reductase inhibitor to a patient in need of such treatment. Statins are the preferred HMG-CoA reductase inhibitors for use in this combination therapy. Preferred statins include lovastatin, simvastatin, pravastatin, fluvastatin, atorvastatin, itavastatin, ZD-4522, rivastatin, and rosuvastatin. This combination treatment may be particularly desirable for treating or reducing the risk of developing atherosclerosis.

Biological Assays

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2

µg/mL benzamidine and 0.5 mM PMSF) containing 0.1% non-fat dry milk and 10 nM [$^3H_2$] AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 µL. Unbound ligand was removed by incubation with 100 µL dextran/gelatin-coated charcoal, on ice, for ~10 min. After centrifugation at 3000 rpm for 10 min at 4° C., 50 µL of the supernatant fraction was counted in a Topcount.

For binding to PPARδ, an aliquot of receptor was incubated in TEGM (10 mM Tris, pH 7.2, 1 mM EDTA, 10% glycerol, 7 µL/100 mL β-mercaptoethanol, 10 mM Na molybdate, 1 mM dithiothreitol, 5 µg/mL aprotinin, 2 µg/mL leupeptin, 2 µg/mL benzamide and 0.5 mM PMSF) containing 0.1% non-fat dry milk and 2.5 nM [$^3H_2$]L-783483, (17 Ci/mmole), ±test compound as described in Berger et al (Novel peroxisome proliferator-activated receptorγ (PPARγ) and PPARδ ligands produce distinct biological effects, 1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 µL. Unbound ligand was removed by incubation with 100 µL dextran/gelatin-coated charcoal, on ice, for ~10 min. After centrifugation at 3000 rpm for 10 min at 4° C., 50 µL of the supernatant fraction was counted in a Topcount.

For binding to PPARα, an aliquot of receptor was incubated in TEGM (10 mM Tris, pH 7.2, 1 mM EDTA, 10% glycerol, 7 µL/100 mL β-mercaptoethanol, 10 mM Na molybdate, 1 mM dithiothreitol, 5 µg/mL aprotinin, 2 µg/mL leupeptin, 2 µg/mL benzamide and 0.5 mM PMSF) containing 0.1% non-fat dry milk and 5.0 nM [$^3H_2$]L-797773, (34 Ci/mmole), +test compound. (L-797733 is (3-(4-(3-phenyl-7-propyl-6-benz-[4,5]-isoxazoloxy)butyloxy))phenylacetic acid, Ex. 62 in WO 97/28137). Assays were incubated for ~16 hr at 4° C. in a final volume of 150 µL. Unbound ligand was removed by incubation with 100 µL dextran/gelatin-coated charcoal, on ice, for ~10 min. After centrifugation at 3000 rpm for 10 min at 4° C., 50 µL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10³ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% $CO_2$. After 24 h, transfections were performed with Lipofectamine (GIBCO BRL, Gaithersburg, Md.) according to the instructions of the manufacturer. Briefly, transfection mixes for each well contained 0.48 µl of Lipofectamine, 0.00075 µg of pcDNA3-PPAR/GAL4 expression vector, 0.045 µg of pUAS(5×)-tk-luc reporter vector and 0.0002 µg of pCMV-lacZ as an internal control for transactivation efficiency. Cells were incubated in the transfection mixture for 5 h at 37° C. in an atmosphere of 10% $CO_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate ±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with a full PPAR agonist, such as rosiglitazone. Generally, if the maximal stimulation of transactivation is less than 50% of the effect observed with a full agonist, then the compound is designated as a partial agonist. If the maximal stimulation of transactivation is greater than 50% of the effect observed with a full agonist, then the compound is designated as a full agonist. The compounds of this invention have EC50 values in the range of 1 nM to 3000 nM.

C) In Vivo Studies

Male db/db mice (10-11 week old C57B1/KFJ, Jackson Labs, Bar Harbor, Me.) are housed 5/cage and allowed ad lib. access to ground Purina rodent chow and water. The animals, and their food, are weighed every 2 days and are dosed daily by gavage with vehicle (0.5% carboxymethylcellulose) ±test compound at the indicated dose. Drug suspensions are prepared daily. Plasma glucose, and triglyceride concentrations are determined from blood obtained by tail bleeds at 3-5 day intervals during the study period. Glucose and triglyceride, determinations are performed on a Boehringer Mannheim Hitachi 911 automatic analyzer (Boehringer Mannheim, Indianapolis, Ind.) using heparinized plasma diluted 1:6 (v/v) with normal saline. Lean animals are age-matched heterozygous mice maintained in the same manner.

EXAMPLES

The following Examples are provided to illustrate the invention and are not to be construed as limiting the invention in any manner. The scope of the invention is defined by the appended claims.

Specific compounds are presented in the Examples and in Table 1, which is provided immediately after the Examples below.

All compounds in Table 1 were analyzed by tandem high pressure liquid chromatography—mass spectrometry (LC-MS) and/or proton NMR. LC-MS samples were analyzed using an Agilent 1100 Series high pressure liquid chromatograph coupled to a Waters Micromass ZQ mass spectrometer. The column used was a Waters XTerra and compounds were eluted using a gradient elution program (10% B to 100% B in 4.5 min) with a flow rate of 2.5 mL/min; Solvent A: water containing 0.06% trifluoroacetic acid; Solvent B: acetonitrile containing 0.05% trifluoroacetic acid. Retention times are given in minutes.

Method A: XTerra MS-C18, 4.5×50 mm, 10-100% B in 4.5 min, flow rate 2.5 ml/min.

Method B: XTerra C18, 3×50 mm, 10-98% in 3.75 min, then 98% for 1 min, flow rate 1 ml/min.

General and specific procedures for making the compounds of this invention and synthetic intermediates are summarized in Schemes 1-9. Other compounds claimed herein can readily be made by a practitioner of medicinal and/or synthetic organic chemistry by adapting the procedures disclosed herein to the specific compound.

Synthesis of Indole Intermediates

Synthesis of Indole Intermediates in which $R^3$ is Benzoyl

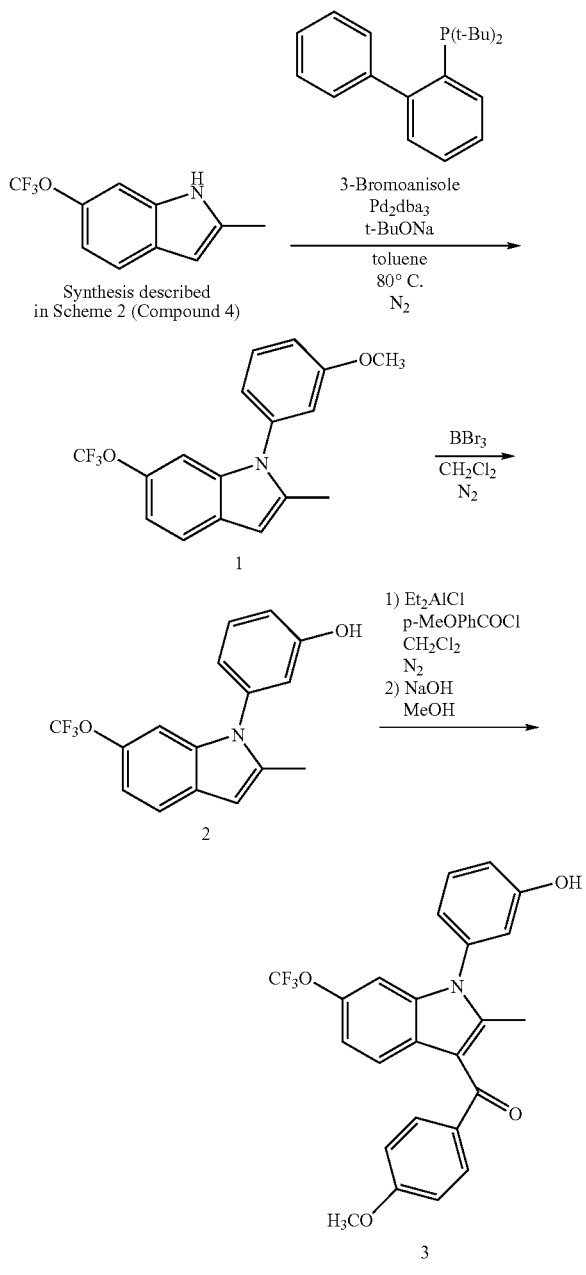

Synthesis of Indole 3, Scheme 1

1-(3-Hydroxy)phenyl-2-methyl-3-(4-methoxy)benzoyl-6-trifluoromethoxyindole (3)

Step 1: 1-(3-methoxy)phenyl-2-methyl-6-trifluoromethoxyindole (1): 2-Methyl-6-trifluoromethoxyindole (645 mg, 3.0 mmole), 3-bromoanisole (0.456 ml, 3.6 mmole), sodium t-butoxide (404 mg, 4.2 mmole), trisdibenzylidine dipalladium (206 mg, 0.225 mmole) and 2-di-t-butylphosphinobiphenyl (201 mg, 0.675 mmole) were stirred in toluene at 80° C. and monitored by TLC (3/1 hexanes/methylene chloride) or reversed phase HPLC until complete. The reaction mixture was then cooled, filtered over celite, and the filtrate evaporated to give a crude isolate, which was purified by silica gel chromatography to give the title compound.

$^1$H NMR (500 MHz, CDCl$_3$): δ 7.53 (d, Ph, 1H), 7.48 (t, Ph, 1H), 7.05 (dd, Ph, 1H), 7.02 (m, Ph, 2H), 6.95 (dd, ph, 1H), 6.89 (t, Ph, 1H), 6.42 (s, Ph, 1H), 3.88 (s, OCH$_3$, 3H), 2.33 (s, 2-CH$_3$, 3H).

Step 2: 1-(3-hydroxy)phenyl-2-methyl-6-trifluoromethoxyindole (2: 460 mg (1.43 mmole) of (1) was dissolved in 7 mL of dichloromethane at 0° C. Boron tribromide (1.0 N, 2.86 mL) in dichloromethane was added, the cooling bath was removed and the reaction was stirred at room temperature overnight. The reaction was then quenched with ice for 30 minutes and partitioned. The organic was washed with water and dried over sodium sulfate. After filtering the drying agent, the filtrate was evaporated and the residue chromatographed over silica gel to give the title compound.

$^1$H NMR (500 MHz, CDCl$_3$): δ 7.51 (d, Ph, 1H), 7.42 (t, Ph, 1H), 7.00 (d, Ph, 1H), 6.98 (s, Ph, 1H), 6.95 (dd, ph, 1H), 6.92 (dd, Ph, 1H), 6.82 (t, Ph, 1H), 6.39 (s, Ph, 1H), 5.03 (s, OH, 1H), 2.31 (s, 2-CH$_3$, 3H).

Step 3: 1-(3-Hydroxy)phenyl-2-methyl-3-(4-methoxy)benzoyl-6-trifluoromethoxyindole (3): 242 mg (0.788 mmole) of (2) was dissolved in methylene chloride (4 ml) and cooled to −20° C. A solution of diethylaluminum chloride in toluene (1.8M, 1.23 ml) was added slowly (over 1-2 minutes) and stirred for 5-15 minutes. Then a solution of 4-methoxybenzoyl chloride (377 mg, 2.21 mmole) in methylene chloride (1 mL) was added, followed by overnight stirring while the reaction slowly reached room temperature. pH 7.0 buffer was added dropwise until gas evolution ceased, then the layers were partitioned. The aqueous layer was extracted twice more with methylene chloride, and then the combined organic layers were washed twice with saturated NaCl solution, dried over sodium sulfate, filtered and evaporated. The crude isolate was then dissolved in methanol (5 mL) and sodium hydroxide solution (1.0 M, 1.6 mL) was added. The reaction was monitored by TLC for disappearance of diacyl indole, then was neutralized with HCl (1.0 M, 1.6 mL). The reaction mixture was then diluted with water and extracted with ethyl acetate. The ethyl acetate layer was dried over sodium sulfate, filtered, evaporated and the residue was chromatographed by silica gel chromatography to give the title compound.

$^1$H NMR (500 MHz, CDCl$_3$): δ 7.84 (d, Ph, 2H), 7.46 (d, Ph, 1H), 7.42 (t, Ph, 1H), 7.06 (dd, Ph, 1H), 6.98 (m, Ph, 3H), 6.95 (s, ph, 1H), 6.92 (dd, Ph, 1H), 6.86 (t, Ph, 1H), 6.38 (s, OH, 1H), 3.91 (s, OCH$_3$, 3H), 2.35 (s, 2-CH$_3$, 3H).

Scheme 2

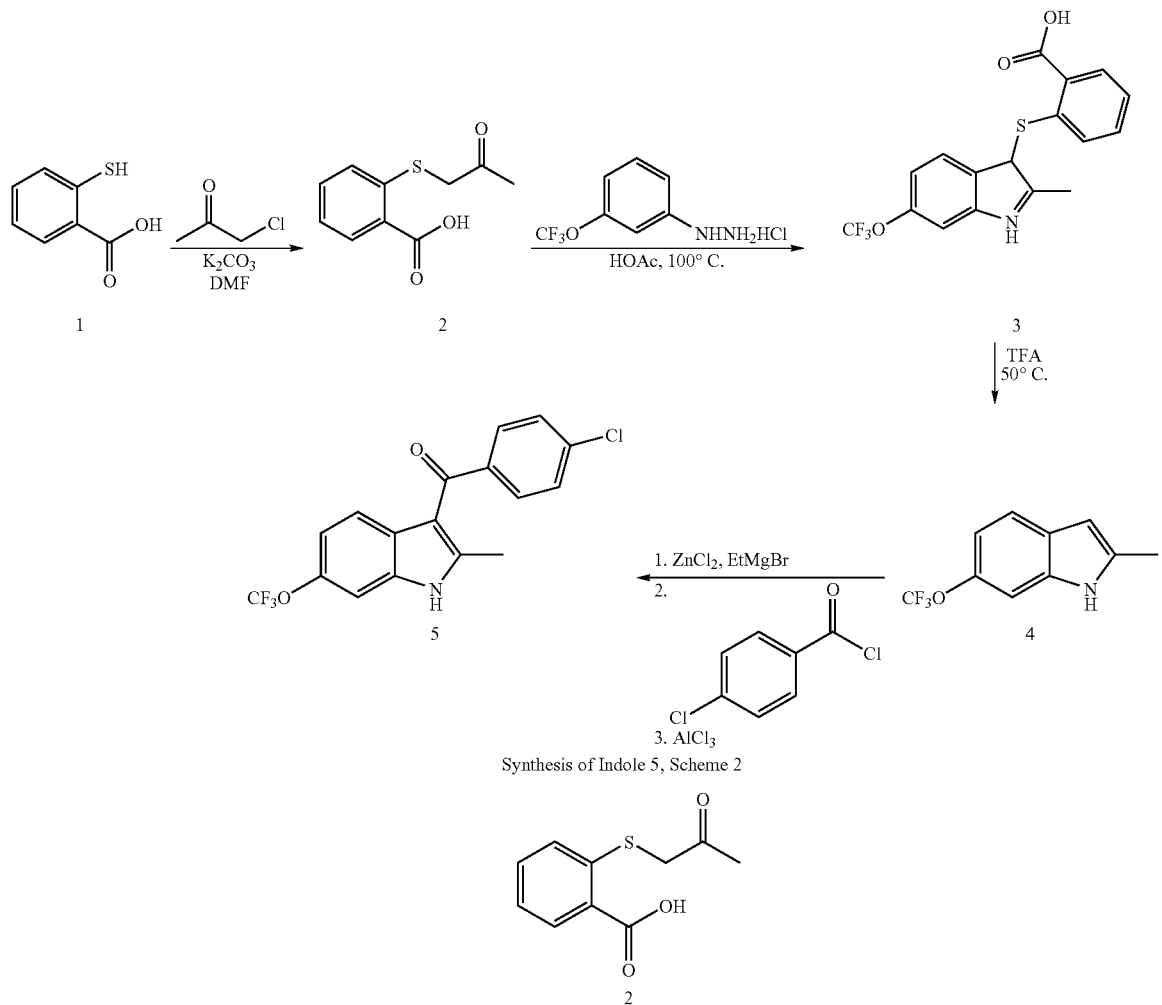

Synthesis of Indole 5, Scheme 2

Ketone 2: A suspension of chloroacetone (6.00 gr, 65 mmol), which was filtered through basic alumina prior to use, phenol 1 (10.00 gr, 65 mmole) and potassium carbonate (8.96 gr, 65 mmol) was stirred in DMF at room temperature under nitrogen atmosphere for 1 h. After this time the reaction was diluted with ethyl acetate/H$_2$O and the layers were separated. The aqueous layer was acidified with 1N HCl and extracted with ethyl acetate (3×). The organic layer was then washed with water (2×), and brine (1×), dried with sodium sulfate, filtered and evaporated to give a pink solid: $^1$H-NMR (CDCl$_3$, 500 MHz) δ 8.14 (t, 1H), 7.53 (t, 1H), 7.35 (d, 1H), 7.27 (d, 1H), 3.78 (s, 2H), 2.35 (s, 3H).

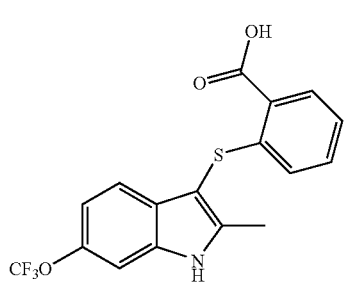

Indole 3: Ketone 2 (1.84 gr, 8.75 mmol) and 4-trifluoromethoxy phenylhydrazine hydrochloride (2.00 gr, 4.76 mmol) were stirred at 100° C. in acetic acid (40 ml, 0.22M) for 1 hour under nitrogen atmosphere to give a 1:2 mixture of 4- and 6-trifluoromethoxy indoles (desired 6-substituted indole is slightly less polar by TLC). The reaction was cooled to room temperature, the acetic acid was removed under reduced pressure and the residue was diluted with ethyl acetate and washed with water (1×) and brine (1×). The organic layer was dried with sodium sulfate, filtered and evaporated to afford 3 as a yellow oil after column chromatography (hexanes/ethyl acetate/1% acetic acid, 6:1); $^1$H-NMR (CDCl$_3$, 500 MHz) δ 8.43 (br s, 1H), 8.16 (dd, 1H), 7.46 (d, 1H), 7.23 (t, 1H), 7.14 (t, 1H), 7.03 (d, 1H), 6.74 (d, 1H), 2.54 (s, 3H).

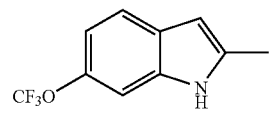

3-H indole 4: A solution of indole 3 (0.29 gr, 0.78 mmol) and thiosalicylic acid (0.12 gr, 0.78 mmol) in trifluoroacetic acid (3 mL, 0.26M) was heated to 50° C. under nitrogen atmosphere for 2 hr. The reaction then was cooled to room temperature, diluted with ethyl acetate and washed with 1N NaOH (2×), and brine (1×). The organic layer was dried with sodium sulfate, filtered and evaporated to afford a brown solid: $^1$H-NMR (CDCl$_3$, 500 MHz) δ 8.01 (br s, 1H), 7.49 (d, 1H), 7.17 (s, 1H), 6.99 (d, 1H), 6.26 (s, 1H), 2.46 (s, 3H).

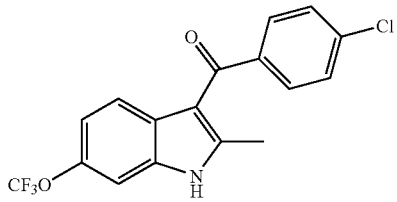

5

3-Acylindole 5: Zinc chloride (0.23 gr, 1.66 mmol) and ethyl magnesium bromide (0.29 ml of a 3M solution in ether, 0.87 mmol) were added to a solution of indole 4 (0.16 gr, 0.74 mmol) in CH$_2$Cl$_2$. The resulting mixture was stirred at room temperature under a nitrogen atmosphere for 1 hr. 4-Chlorobenzoyl chloride (0.21 gr, 1.18 mmol) was then added and stirring was continued for 1 hr. Finally, aluminum chloride (0.053 gr, 0.39 mmol) was added and the reaction mixture was stirred for 3 hr. After this time, the reaction was quenched with NH$_4$Cl(aq), diluted with CH$_2$Cl$_2$, washed with 1N NaOH (1×) and brine (3×). The organic layer was dried with sodium sulfate, filtered and evaporated to afford a light yellow oil after column chromatography (hexanes/ethyl acetate, 4:1); $^1$H-NMR (CDCl$_3$, 500 MHz) δ 8.54 (br s, 1H), 7.73 (d, 2H), 7.48 (d, 2H), 7.40 (d, 1H), 7.24 (s, 1H), 7.02 (d, 1H), 2.60 (s, 3H).

Synthesis of an Indole Intermediate where R$^3$ is Phenoxy

Compounds in which R$^3$ is phenoxy or thiophenoxy can be made from an indole intermediate having a phenoxy or thiophenoxy substituent in the 3-position. The synthesis of such an intermediate is shown in the scheme below, which is followed by a detailed description of the synthetic steps. Other compounds in Table 1 having phenoxy or thiophenoxy substituents in the R$^3$ position can be synthesized by one of ordinary skill in the art by using similar synthetic strategies and readily available materials.

Scheme 3

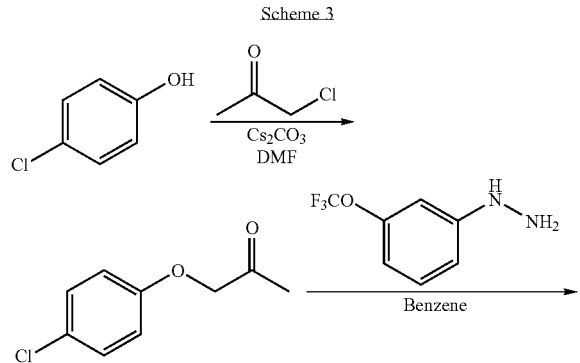

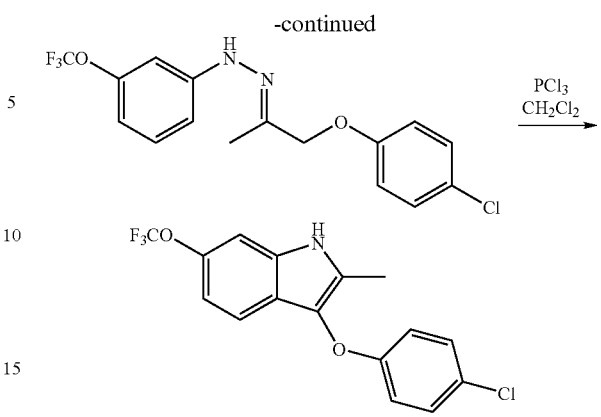

Synthesis of
3-(4-Chlorophenoxy)-5-trifluoromethoxyindole
Product of Scheme 3

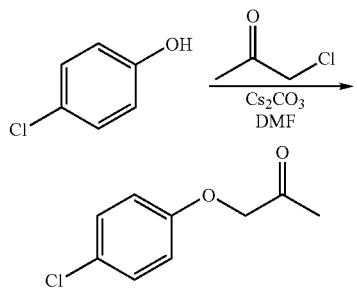

To a solution of 4-chlorophenol (15.36 g) in DMF (150 mL) at room temperature was added Cs$_2$CO$_3$ (64.4 g). After 15 min, chloroacetone (14.8 mL) was introduced via syringe. The reaction mixture was stirred for 3 hours, then partitioned between ether and water. The organic layer was washed sequentially with water, 1N aqueous NaOH solution (2×), and brine, dried over anhydrous MgSO$_4$, filtered, and concentrated in vacuo. Distillation under high vacuum gave the product as slightly yellow oil. $^1$H NMR (CDCl$_3$, 500 MHz) δ 7.28 (d, 2H), 6.83 (d, 2H), 4.54 (s, 2H), 2.29 (s, 3H).

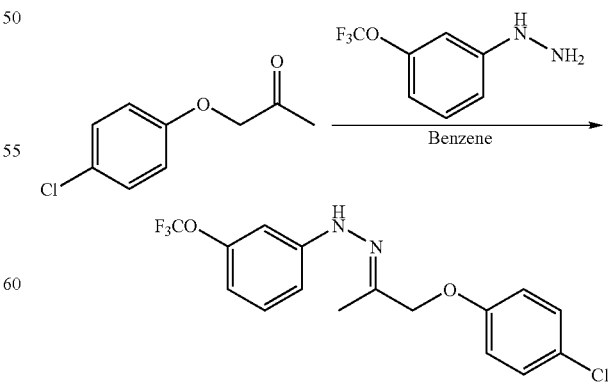

The above obtained ketone (12.89 g) and 3-trifluoromethoxyphenyl hydrazine (12.22 g) were dissolved in benzene (50 mL). The reaction mixture was heated at 60° C. for 45 min, cooled to room temperature, dried over anhydrous Na₂SO₄, filtered, and concentrated in vacuo to give the phenylhydrazone, which was used immediately without further purification.

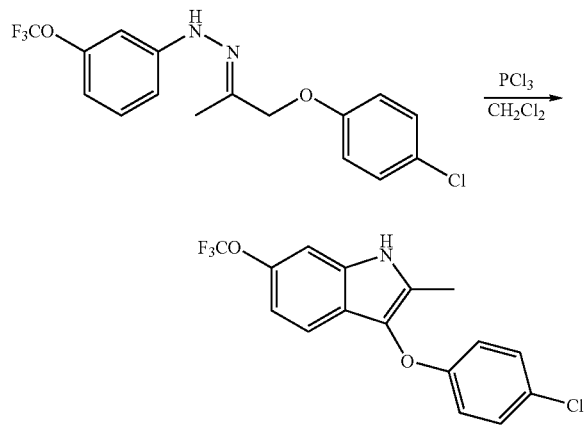

To a solution of the above obtained hydrazone (23 g) in CH₂Cl₂ (200 mL) at room temperature was added PCl₃ (11 mL). The reaction was stirred at room temperature for 24 h before water (3 mL) was introduced and the reaction was vigorously stirred for another 15 min. After cooling to 0° C. by an ice-water bath, the reaction was neutralized to pH 7 by adding 5N aqueous NaOH solution. Most of the solvent was removed in vacuo. The residue was partitioned between ether and water. The organic layer was washed with water and brine, dried over anhydrous MgSO₄, filtered, and concentrated in vacuo. Purification by flash chromatography (SiO₂, EtOAc/hex 25/1) gave the desired product along with the corresponding 4-trifluoromethoxyindole isomer. ¹H NMR (CDCl₃, 500 MHz) δ 7.80 (s, broad, 1H), 7.24 (d, J=8.7 Hz, 2H), 7.22 (d, J=8.4 Hz, 1H), 7.19 (s, 1H), 6.95 (d, J=8.4 Hz, 1H), 6.91 (d, J=8.7 Hz, 2H), 2.35 (s, 3H).

Synthesis of an Indole Intermediate in which R³ is Benzisoxazole

The synthesis of an indole intermediate compound in which R³ is benzisoxazole is shown in Scheme 4 below. The procedure is described in detail immediately after Scheme 4. Compounds in which R³ is benzisoxazole are included in Table 1. These can be made by a skilled practitioner in synthetic organic chemistry using the methods and strategies disclosed herein.

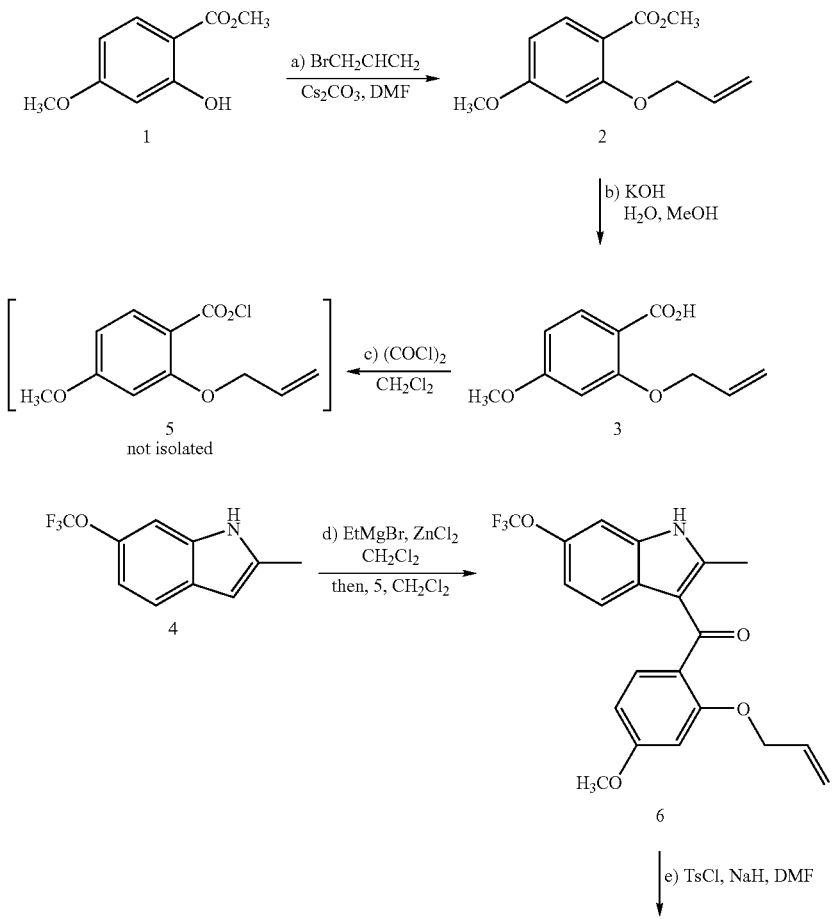

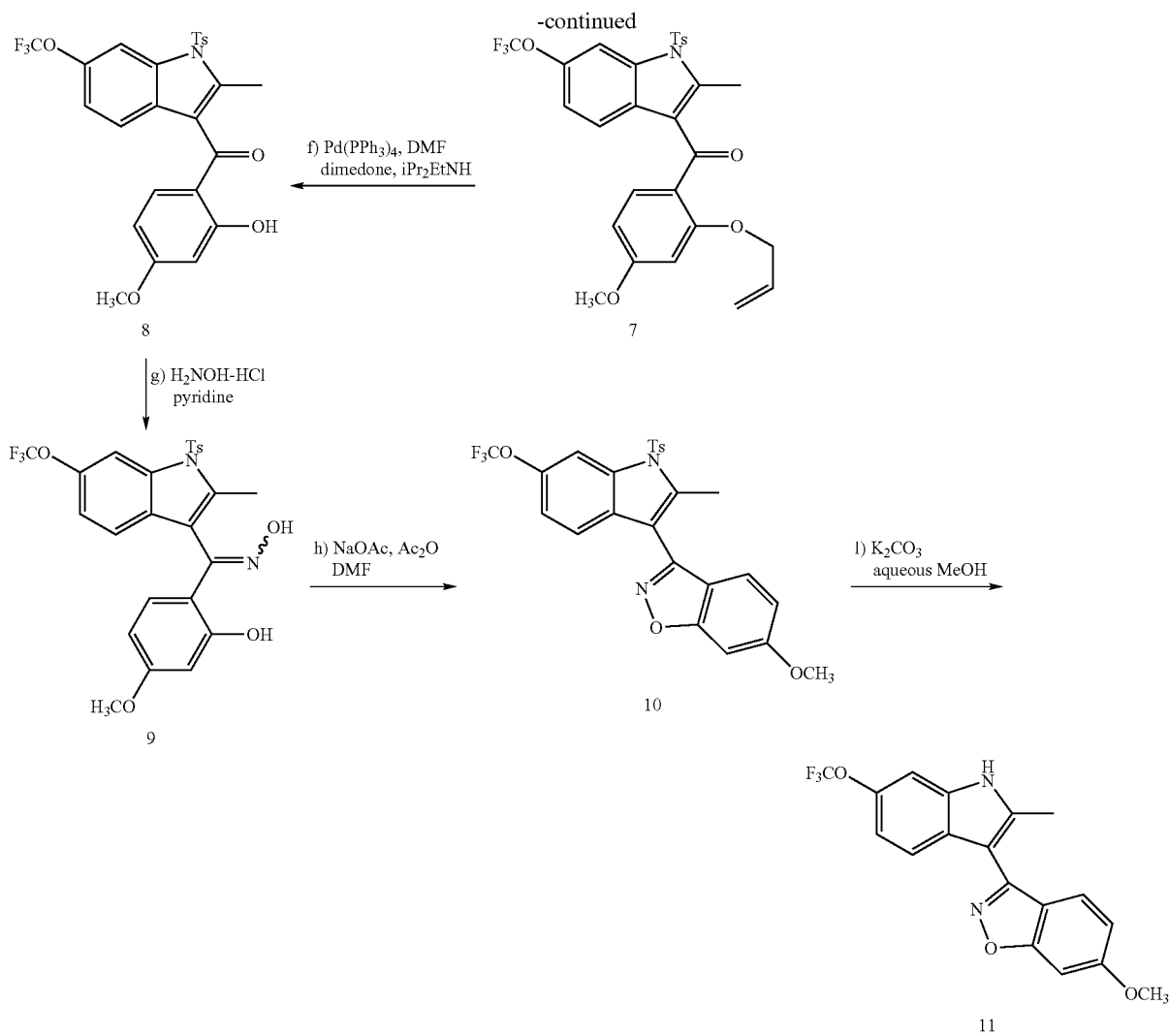

6-Methoxy-3-[2-methyl-6-(trifluoromethoxy)-1H-indol-3-yl]-1,2-benzisoxazole (11)

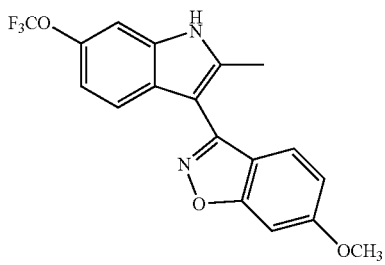

Step 1. Methyl 2-(allyloxy)-4-methoxybenzoate (2)

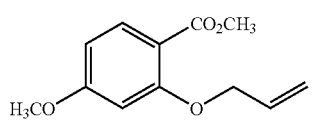

To a solution of methyl 4-methoxysalicylate (2.0 g, 11 mmol) in DMF (20 mL) at room temperature was added $Cs_2CO_3$ (1.3 eq, 4.7 g) and allyl bromide (1.3 eq, 1.23 mL). After 2 hr, reaction mixture was diluted with EtOAc and washed with water (3×), brine (1×). The organic layer was dried over $Na_2SO_4$ and concentrated to provide the product as a pale yellow oil. Product was used without further purification.

$^1$H NMR (500 MHz, $CDCl_3$): δ 7.89 (d, 1H), 6.53 (dd, 1H), 6.49 (d, 1H), 6.08 (m, 1H), 5.55 (d, 1H), 5.33 (d, 1H), 4.63 (d, 2H), 3.89 (s, 3H), 3.86 (s, 3H).

Step 2. 2-(allyloxy)-4-methoxybenzoic acid (3)

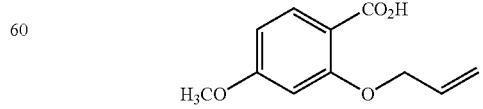

To a solution of 2 (20.5 g, 11 mmol) in aqueous methanol (30 mL) was added KOH (1 eq, 630 mg). Reaction was heated to 50° C. for 12 hours before the addition of more KOH (630 mg). After 12 hours, the mixture was cooled, diluted with EtOAc and washed with 1M HCl. Aqueous layer was extracted with EtOAc (3×). Combined organic layers, dried over Na$_2$SO$_4$, and concentrated. Product was isolated as an off white solid and used without further purification.

$^1$H NMR (500 MHz, CD$_3$OD): δ 7.85 (d, 1H), 6.60 (m, 2H), 6.08 (m, 1H), 5.49 (d, 1H), 5.30 (d, 1H), 4.68 (d, 2H), 3.84 (s, 3H).

Step 3. [2-(allyloxy)-4-methoxyphenyl][2-methyl-6-(trifluoromethoxy)-1H-indol-3-yl]methanone (6)

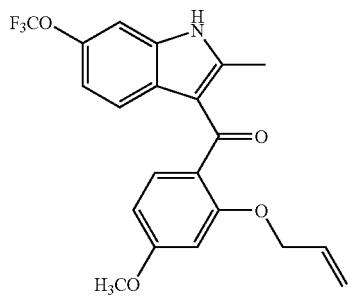

To a slurry of 4 (6.34 g, 29 mmol) and ZnCl$_2$ (2.1 eq, 8.3 g) in CH$_2$Cl$_2$ (220 mL) at ambient temperature was added EtMgBr (3.0M in ether). In a separate flask, oxallyl chloride (1.3 eq, 3.3 mL) was added to a solution of 3 (1.1 eq, 6.8 g) in CH$_2$Cl$_2$ (200 mL). After 1 hour, the newly formed acid chloride (5) solution was added via cannula to the indole. The reaction stirred for 1 hour before being quenched by pouring into a solution of satd NH$_4$Cl. Layers were allowed to separate and then the organic layer was washed with NH$_4$Cl (2×) and NaHCO$_3$ (2×). The organic layer was dried over Na$_2$SO$_4$ before being filtered through a pad of silica gel, eluting with 2:1 CH$_2$Cl$_2$/EtOAc. The filtrate was concentrated to provide a red solid which was triturated with MeOH (50-100 mL). The mother liquor was concentrated and the process repeated. Product was isolated as a colored solid.

$^1$H NMR (500 MHz, CDCl$_3$): δ 8.48 (bs, 1H), 7.45 (d, 1H), 7.40 (d, 1H), 7.16 (s, 1H), 6.97 (d, 1H), 6.60 (d, 1H), 6.52 (d, 1H), 5.67 (m, 1H), 5.03 (d, 1H), 5.00 (s, 1H), 4.40 (d, 2H), 3.89 (s, 3H), 2.54 (s, 3H).

Step 4. [2-(Allyloxy)-4-methoxyphenyl][2-methyl-1-[(4-methylphenyl)sulfonyl]-6-(trifluoromethoxy)-H-indol-3-yl]methanone (7)

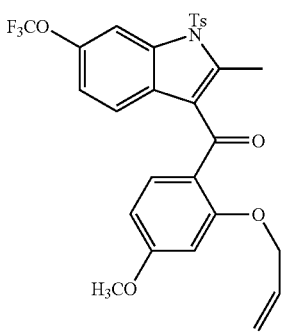

To a solution of 6 (80.0 g, 20 mmol) in DMF (200 mL) was added NaH (1.5 eq). The mixture was stirred for 15 min before addition of TsCl (1.5 eq, 5.6 g). After 1 hour, the reaction mixture was poured into ice water and extracted with CH$_2$Cl$_2$. The organic layer was washed with NH$_4$Cl (2×), NaHCO$_3$ and brine, then dried with Na$_2$SO$_4$ and concentrated. Purification via flash chromatography eluting with 20% EtOAc/hexanes afforded the product as a viscous yellow oil.

$^1$H NMR (500 MHz, CDCl$_3$): δ 8.17 (s, 1H), 7.75 (d, 2H), 7.58 (d, 1H), 7.29 (d, 2H), 7.24 (d, 1H), 7.05 (d, 1H), 6.60 (dd, 1H), 6.42 (d, 1H), 5.41 (m, 1H), 4.91 (m, 2H), 4.20 (d, 2H), 3.89 (s, 3H), 2.70 (s, 3H), 2.41 (s, 3H).

Step 5. (2-Hydroxy-4-methoxyphenyl)[2-methyl-1-[(4-methylphenyl)sulfonyl]-6-(trifluoromethoxy)-1H-indol-3-yl]methanone (8)

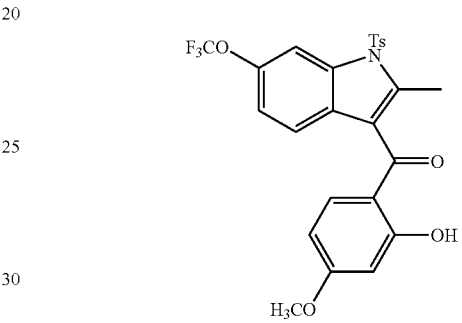

To a solution of 7 (9.0 g, 16 mmol), dimedone (1.5 eq, 3.4 g), and Pd(PPh$_3$)$_4$ (5 mol %, 930 mg) in DMF (160 mL) was added diisopropylethylamine (1.5 eq, 4.2 mL). After 30 min, the reaction mixture was diluted with DCM and washed with 0.05M HCl (3×), NaHCO$_3$, and brine. The organic layer was dried with Na$_2$SO$_4$ then filtered through a pad of silica gel to remove remaining palladium. Product was purified via flash chromatography eluting with 14% EtOAc/hexanes to provide the product as an amorphous yellow solid contaminated with ~10% allylated dimedone. Product was used without further purification.

$^1$H NMR (500 MHz, CDCl$_3$): δ 12.66 (s, 1H), 8.20 (s, 1H), 7.77 (d, 2H), 7.32 (d, 1H), 7.30 (m, 3H), 7.14 (d, 1H), 6.52 (d, 1H), 6.37 (dd, 1H), 3.89 (s, 3H), 2.63 (s, 3H), 2.42 (s, 3H).

Step 6. (2-Hydroxy-4-methoxyphenyl)[2-methyl-1-[(4-methylphenyl)sulfonyl]-6-(trifluoromethoxy)-1H-indol-3-yl]methanone oxime (9)

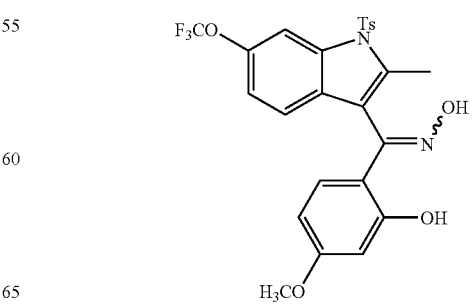

A solution of 8 (16 mmol), hydroxylamine hydrochloride (10 eq, 11.2 g) and pyridine (270 mL) was heated to 80° C. for 24 hours. Additional hydroxylamine (3 g) was added and the temperature was increased to 90° C. After LC analysis confirmed the consumption of starting material, the reaction was cooled and the pyridine removed by rotary evaporation. The residue was dissolved in DCM and washed with water and 1M HCl. The organic layer was dried over $Na_2SO_4$ and concentrated. The reaction mixture was purified by flash chromatography eluting with 20% EtOAc/hexanes, Rf=0.4. The product was isolated as a white foam.

$^1$H NMR (500 MHz, $CDCl_3$): δ 8.15 (s, 1H), 7.71 (d, 2H), 7.45 (bs, 1H), 7.27 (d, 2H), 7.09 (m, 2H), 6.56 (m, 2H), 6.23 (dd, 1H), 3.79 (s, 3H), 2.47 (s, 3H), 2.40 (s, 3H).

Step 7. 6-Methoxy-3-[2-methyl-1-[(4-methylphenyl)sulfonyl]-6-(trifluoromethoxy)-1H-indol-3-yl]-1,2-benzisoxazole (10)

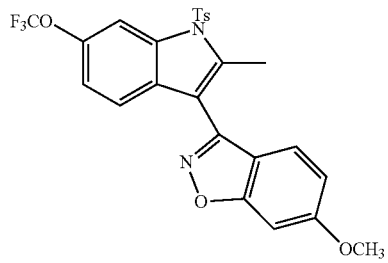

To a solution of 9 (3.8 g, 7.1 mmol) and NaOAc (3 eq, 1.8 g) in DMF (120 mL) was added $Ac_2O$ (3 eq, 2 mL). The reaction was heated to 110° C. for 4 hours at which time no starting material was detected by LC analysis. The reaction was cooled and diluted with DCM. The solution was washed with $NH_4Cl$, brine and $NaHCO_3$, then dried over $Na_2SO_4$ and concentrated. The residue was purified via flash chromatography eluting with 20% EtOAc/hexanes. Product was isolated as white foam.

$^1$H NMR (500 MHz, $CDCl_3$): δ 8.23 (s, 1H), 7.77 (d, 2H), 7.48 (d, 1H), 7.36 (d, 1H), 7.28 (d, 2H), 7.15 (d, 1H), 7.09 (d, 1H), 6.94 (dd, 1H), 3.92 (s, 3H), 2.74 (s, 3H), 2.39 (s, 3H).

Step 8. 6-Methoxy-3-[2-methyl-6-(trifluoromethoxy)-1H-indol-3-yl]-1,2-benzisoxazole (11)

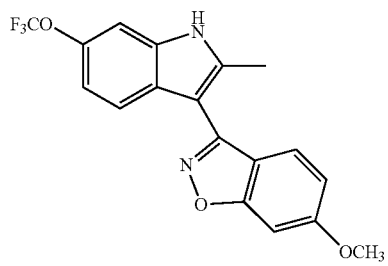

$K_2CO_3$ (3 eq) and 10 (2.5 g, 4.8 mmol) were heated to reflux in aqueous methanol for 2 hours at which time starting material had been consumed. The reaction mixture was concentrated, diluted with EtOAc and washed with brine. The organic layer was dried over $Na_2SO_4$ and concentrated. The residue was purified via flash chromatography eluting with 20% EtOAc/hexanes to provide the product as a pale green solid.

$^1$H NMR (500 MHz, $CDCl_3$): δ 8.45 (bs, 1H), 7.62 (d, 1H), 7.56 (d, 1H), 7.25 (s, 1H), 7.09 (d, 1H), 7.05 (d, 1H), 6.94 (dd, 1H), 3.93 (s, 3H), 2.63 (s, 3H).

Synthesis of an Indole Intermediate in which $R^3$ is Phenyl

A synthetic method is shown below for an intermediate in which $R^3$ is phenyl. Compounds of this invention in which $R^3$ is phenyl are included in the compounds shown in Table 1. The compounds in Table 1 in which $R^3$ is phenyl were synthesized using the methods and strategies described herein, readily available materials, and synthetic methods well known to practitioners in the field of synthetic organic chemistry. Such synthetic methods and materials are readily apparent to practitioners in the field of synthetic organic chemistry.

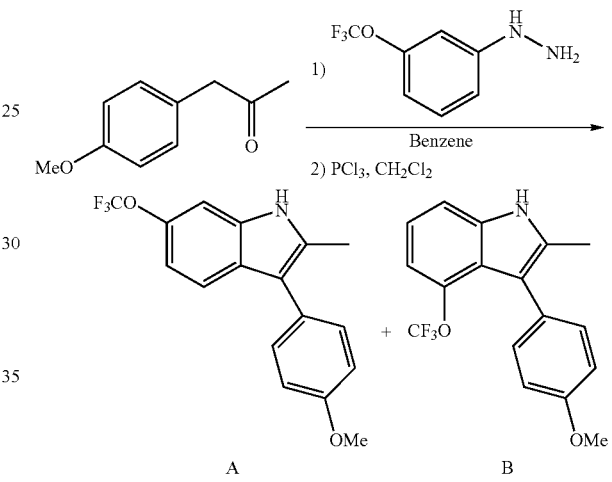

4-Methoxyphenylacetone (1.12 g) and 3-trifluoromethoxyphenyl hydrazine (0.96 g) were dissolved in benzene (20 mL). The reaction mixture was heated at 60° C. for 45 min, cooled to room temperature, dried over anhydrous $Na_2SO_4$, filtered, and concentrated in vacuo to give the phenylhydrazone, which was used immediately without further purification.

To a solution of the above obtained hydrazone (2.0 g) in $CH_2Cl_2$ (100 mL) at room temperature was added $PCl_3$ (0.76 mL). The reaction was stirred at room temperature for 24 h. After cooling to 0° C. by an ice-water bath, the reaction was neutralized to pH 7 by adding 5N aqueous NaOH solution. Most of the solvent was removed in vacuo. The residue was partitioned between ether and water. The organic layer was washed with water and brine, dried over anhydrous $MgSO_4$, filtered, and concentrated in vacuo. Purification by flash chromatography ($SiO_2$, EtOAc/hex 25/1) gave 6-trifluoromethoxy product A along with the corresponding 4-trifluoromethoxyindole isomer B.

Isomer A: $^1$H NMR ($CDCl_3$, 500 MHz) δ 8.01 (s, broad, 1H), 7.56 (d, J=8.7 Hz, 1H), 7.40 (d, J=8.6 Hz, 2H), 7.20 (s, 1H), 7.02 (d, J=8.7 Hz, 2H), 6.99 (d, J=8.7 Hz, 1H), 3.88 (s, 3H), 2.49 (s, 3H).

Isomer B: $^1$H NMR ($CDCl_3$, 500 MHz) δ 8.09 (s, broad, 1H), 7.31 (d, J=8.7 Hz, 2H), 7.26 (d, J=8.6 Hz, 1H), 7.1 (t, J=8.0 Hz, 1H), 6.96 (overlapping signals, 3H), 3.87 (s, 3H), 2.39 (s, 3H).

Scheme 5
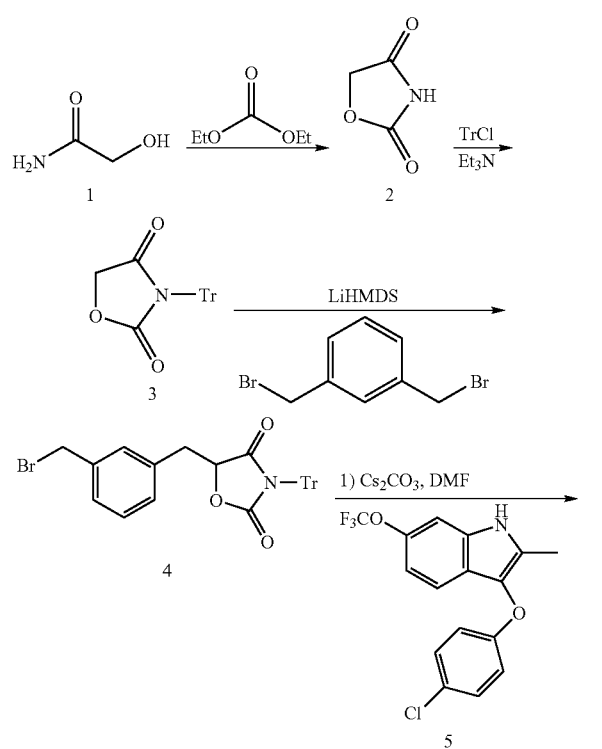
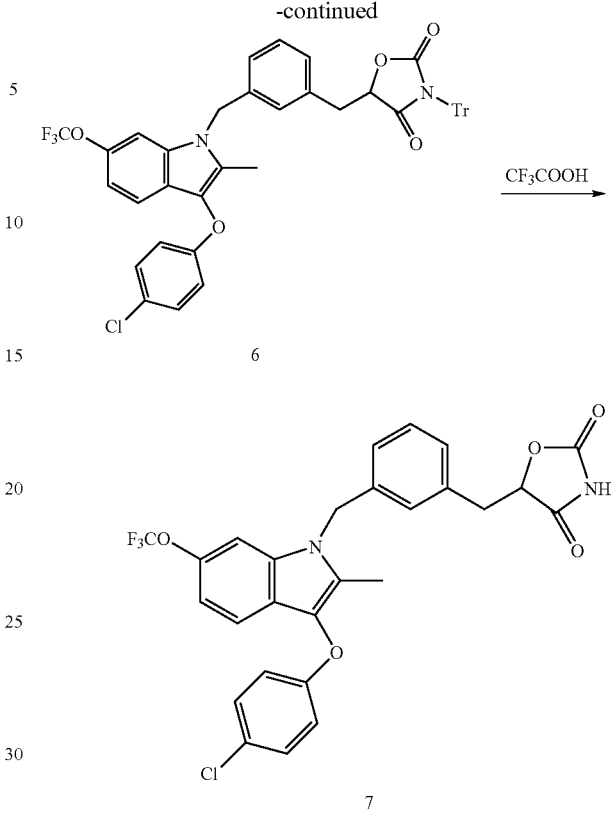
Scheme 6
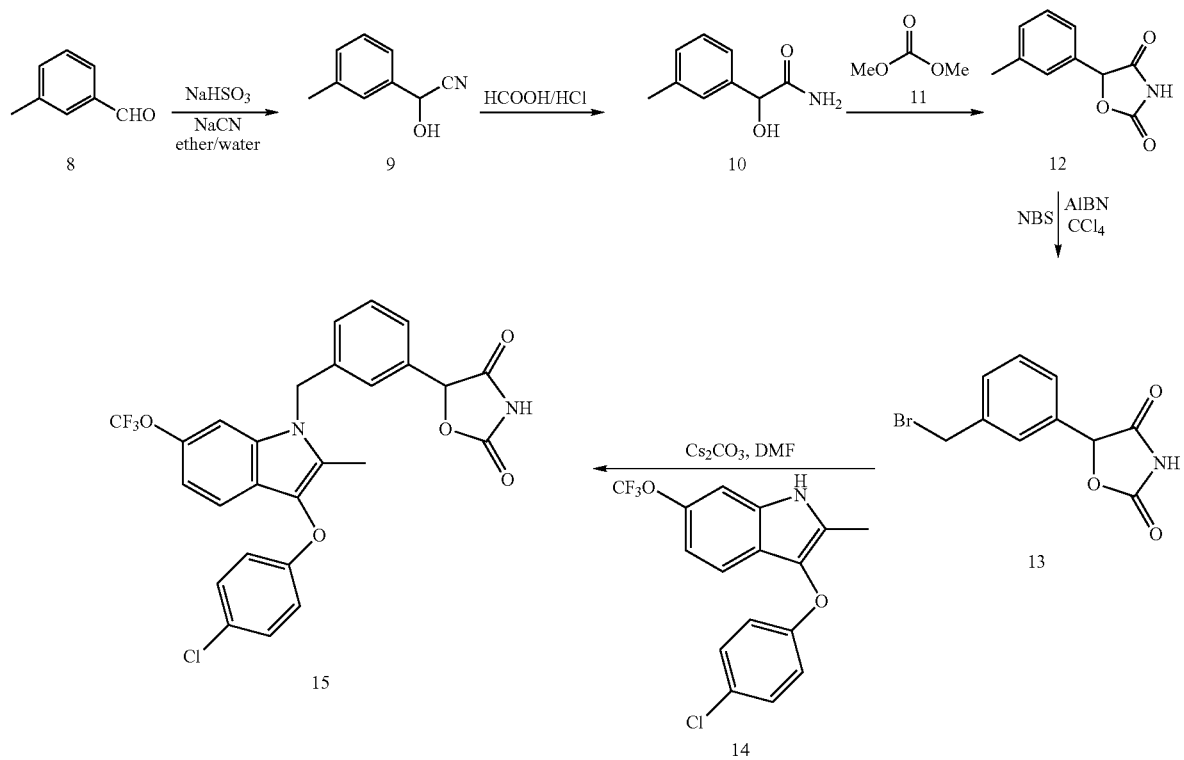

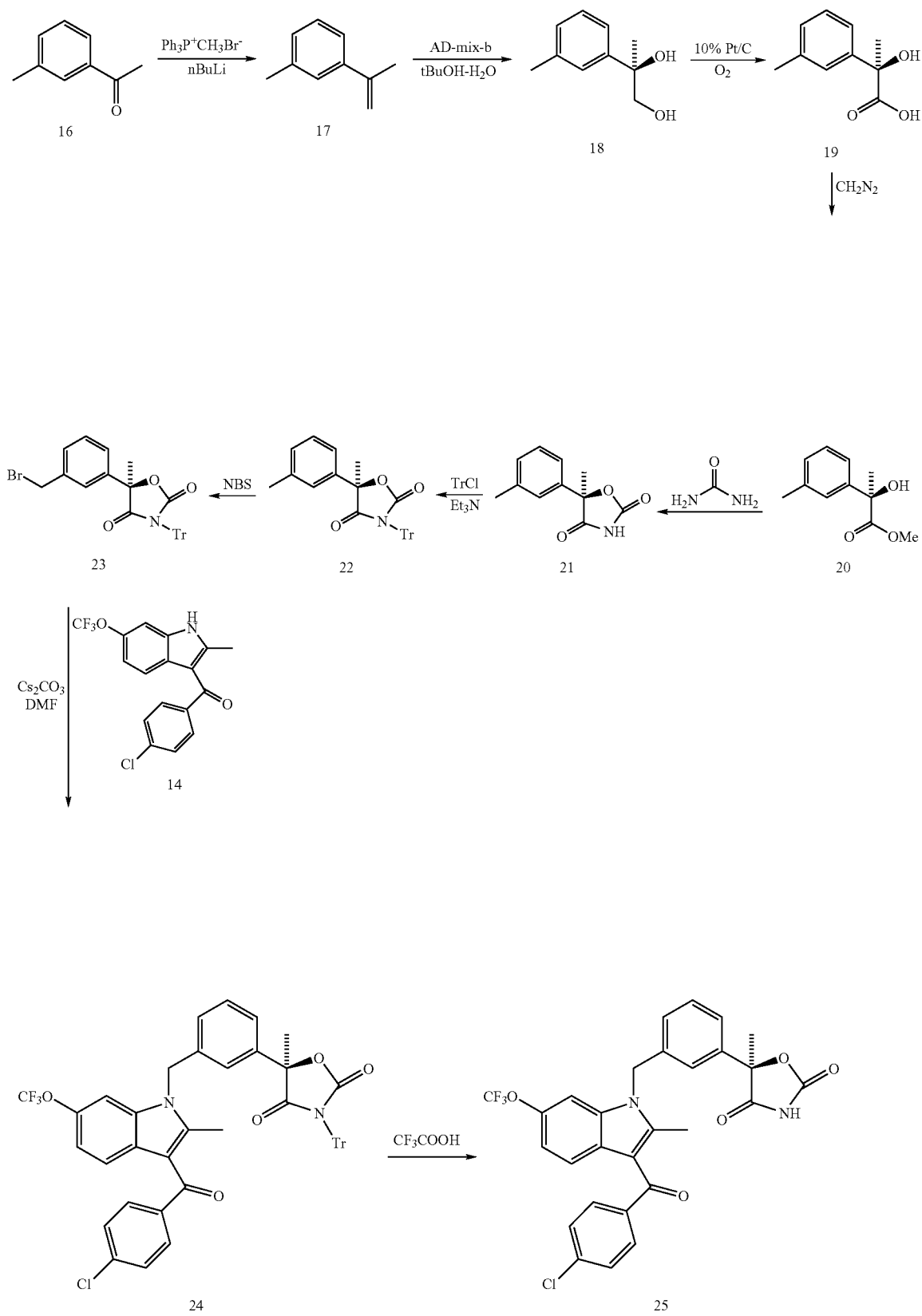
Scheme 7.

Scheme 8.

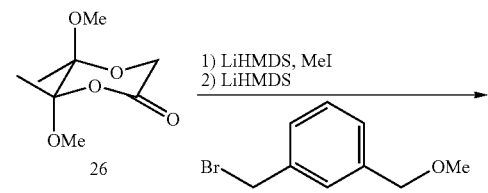

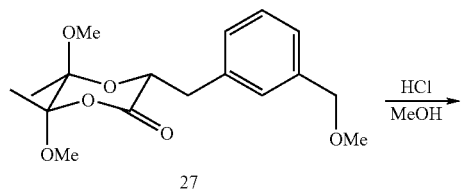

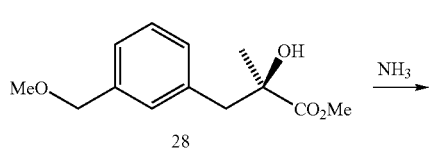

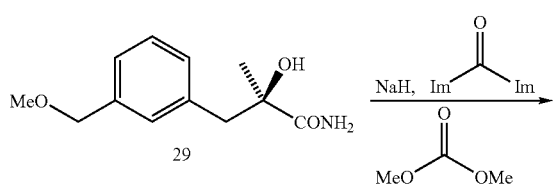

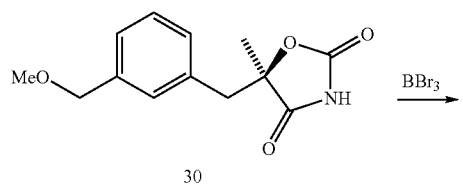

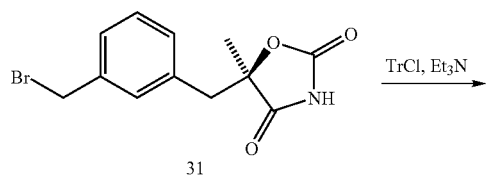

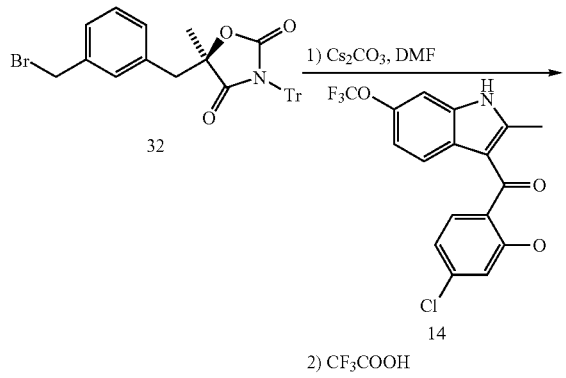

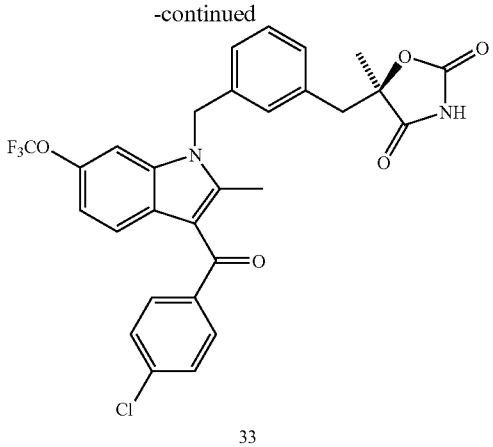

33

Example 1

See Scheme 5

Step 1. Preparation of Intermediate 4

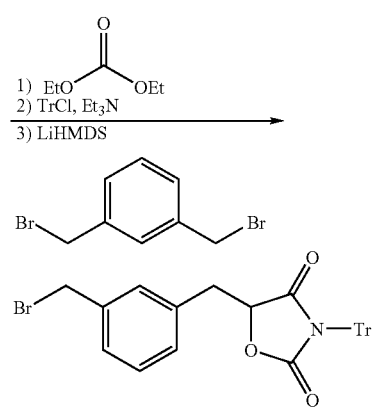

4

To a solution of glycolamide (14 g, 186 mmol) and diethyl carbonate (27.1 mL, 224 mmol) in methanol (200 mL) was added potassium t-butoxide (20.8 g, 186 mmol). The reaction mixture was refluxed overnight, then cooled to room temperature. The solvent was removed in vacuo. The residue was dissolved in brine, acidified with 2N HCl, then extracted with EtOAc. The organic layer was washed with brine, dried over $Na_2SO_4$, filtered, and concentrated in vacuo to give 8.0 g of oxazolidinedione as a white solid.

To a solution of the above obtained oxazolidinedione (4.6 g, 45 mmol) in $CH_2Cl_2$ (50 mL) were added TrCl (12.6 g, 45 mmol) and $Et_3N$ (6.3 mL, 45 mmol). The reaction mixture was stirred at room temperature for 40 min, then partitioned between water and EtOAc. The organic layer was washed with water and brine, dried over $Na_2SO_4$, filtered, and concentrated in vacuo to give the N-trityl OZD product.

To a solution of the above obtained N-trityl OZD (2.53 g, 7.37 mmol) in THF (50 mL) at −78° C. were added LiHMDS (1.0 N in THF, 8.85 mL, 8.85 mmol) and HMPA (1.55 mL, 8.85 mmol). After 10 min at −78° C., dibromoxylene was added. The reaction was stirred for 30 min, quenched with saturated NH₄Cl solution, then partitioned between water and ether. The organic layer was washed with water and brine, dried over Na₂SO₄, filtered, and concentrated in vacuo. Purification by flash chromatography gave the product.

¹H NMR (500 MHz, CDCl₃) δ 7.5-7.0 (overlapping signals, 19H), 4.90 (t, J=4.5 Hz, 1H), 4.54 (s, 2H), 3.36 (dd, J=4.5, 14.5 Hz, 1H), 3.18 (dd, J=4.5, 14.5 Hz, 1H).

Step 2. Preparation of OZD 7

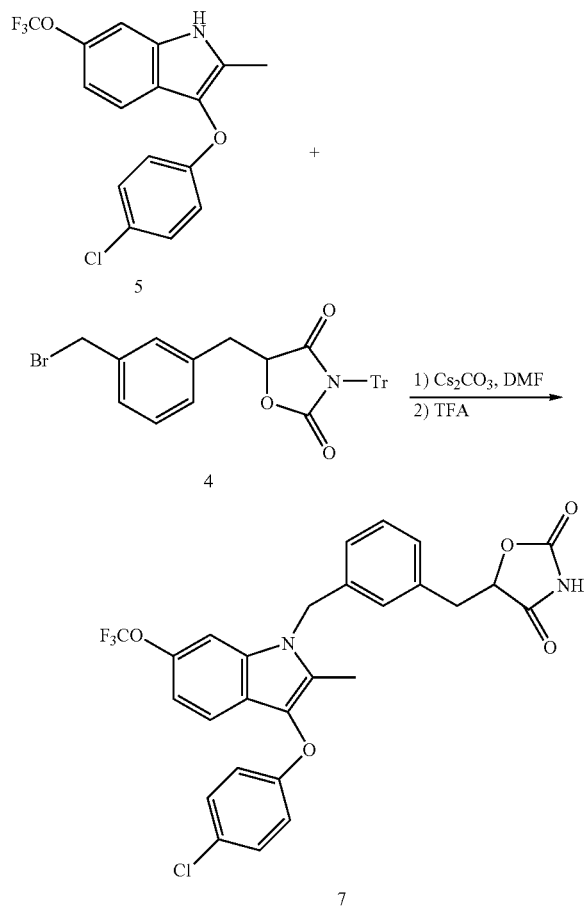

To a solution of indole 5, which was made according to Scheme 3, (200 mg, 0.58 mmol) in DMF (5 mL) at room temperature were added bromide 4 (305 mg, 0.58 mmol) and Cs₂CO₃ (284 mg, 0.87 mmol). The reaction was stirred for 5 h, then partitioned between water and diethyl ether. The organic layer was washed with brine, dried over Na₂SO₄, filtered, and concentrated in vacuo. Purification by flash chromatography gave the coupling product.

To a solution of the above obtained product in CH₂Cl₂ (10 mL) was added trifluoroacetic acid (2 mL). The reaction mixture was stirred at room temperature for 0.5 h, then evaporated to dryness in vacuo. The residue was purified by flash chromatography to give 7.

¹H NMR (500 MHz, CDCl₃) δ 7.51 (s, broad, 1H), 7.30-7.24 (overlapping signals, 4H), 7.18 (d, J=7.6 Hz, 1H), 7.09 (s, 1H), 6.96-6.92 (overlapping signals, 4H), 5.29 (s, 2H), 5.08 (t, J=4.8 Hz, 1H), 3.30 (dd, J=4.3, 14.5 Hz, 1H), 3.17 (dd, J=4.3, 14.5 Hz, 1H), 2.27 (s, 3H).

Example 2

See Scheme 6

Step 1. Preparation of Intermediate 13

To a solution of NaHSO₃ (10.7 g, 103 mmol) in water (150 mL) at 50° C. was added aldehyde 8 (19.3 g, 86 mmol). The reaction was stirred for 1.5 h at 50° C., then cooled to 0° C. Et₂O (100 mL) was added, followed by a suspension of NaCN (4.66 g) in water (100 mL). After 2 h at 0° C., the layers were separated. The aqueous layer was extracted with ether. The combined organic layers were washed with brine, dried over Na₂SO₄, filtered, and concentrated in vacuo to give the cyanohydrin product as an oil.

To a solution of the product obtained above (10 g) in HCOOH (30 mL) at 0° C. was added slowly concentrated HCl (30 mL). The reaction was stirred at 0° C. for 2 h, poured over crushed ice, extracted with EtOAc (2×). The combined organic layers were washed with water, 1.0 N NaOH aqueous solution (3×), brine, dried over Na₂SO₄, filtered, and concentrated in vacuo to give the amide as white solid.

To a solution of the amide obtained above (5.3 g, 32 mmol) in tBuOH (85 mL) were added KOBut (7.18 g, 64 mmol) and dimethyl carbonate (5.4 mL, 64 mmol). The reaction mixture was refluxed for 4 h, cooled to room temperature, acidified with HCl (1.0N, 65 mL), partitioned between water and CH₂Cl₂. The organic layer was washed with water and brine, dried over Na₂SO₄, filtered, and concentrated in vacuo. The residue was crystallized from Et₂O/hexanes to give the OZD product as white solid.

To a solution of the above obtained OZD (0.96 g, 5.02 mmol) in CCl₄ (30 mL) were added NBS (0.89 g, 5.02 mmol) and catalytic amount of AIBN. The reaction was refluxed overnight, cooled to room temperature, filtered, and concentrated in vacuo. Purification by chromatography gave the benzyl bromide product 13.

¹H NMR (500 MHz, CDCl₃) δ 7.52 (s, broad, 1H), 7.6-7.4 (overlapping signals, 4H), 5.85 (s, 1H), 4.54 (s, 2H).

Step 2. Preparation of OZD 15

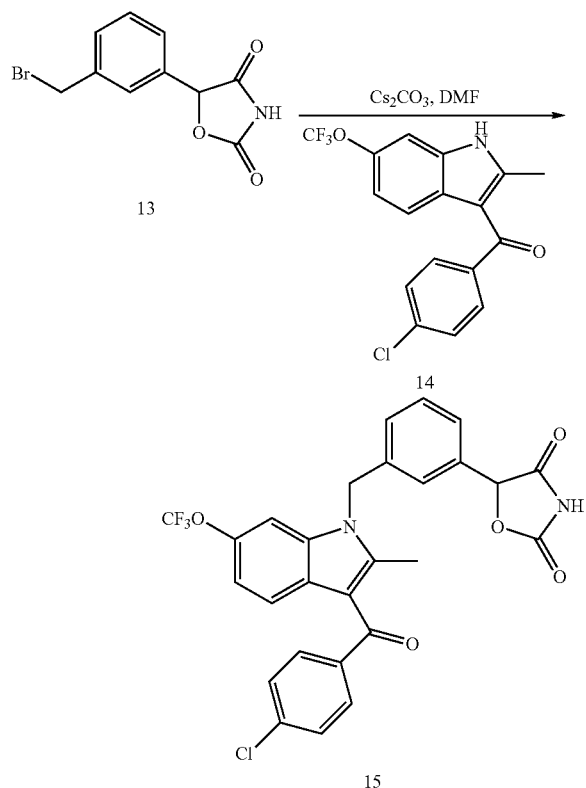

To a solution of indole 14, which is Compound 5 of Scheme 2 (45 mg, 0.127 mmol), in DMF (5 mL) at room temperature were added bromide 13 (65 mg, 0.127 mmol) and Cs₂CO₃ (85 mg, 0.26 mmol). The reaction was stirred for 5 h, partitioned between water and diethyl ether. The organic layer was washed with brine, dried over Na₂SO₄, filtered, and concentrated in vacuo. Purification by flash chromatography gave the coupling product 15.

¹H NMR (500 MHz, CDCl₃) δ 8.25 (s, broad, 1H), 7.77 (d, J=8.4 Hz, 2H), 7.49 (d, J=8.4 Hz, 2H), 7.41 (overlapping signals, 3H), 7.24 (s, 1H), 7.13 (s, 1H), 7.02 (overlapping signals, 2H), 5.80 (s, 1H), 5.43 (s, 2H), 2.54 (s, 3H).

Example 3

See Scheme 7

Step 1. Preparation of (R)-diol 18

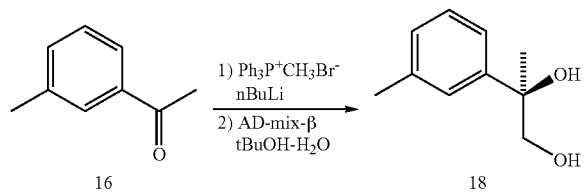

To a suspension of methyltriphenylphosphonium bromide (33.2 g, 92.9 mmol) in diethyl ether (200 mL) at room temperature was added slowly nBuLi (2.5 M in hexanes, 37 mL). The resulting yellow solution was stirred for 30 min before ketone 16 (12 mL, 90 mmol) was introduced. The reaction was stirred at room temperature overnight. The precipitate was removed by filtration. The solvent was removed in vacuo. Purification by flash chromatography gave the alkene product.

To a suspension of AD-mix-β (7 g) in H₂O/tBuOH (25 mL/25 mL) at 0° C. was added the above obtained alkene (0.66 g, 5 mmol). The reaction mixture was stirred at 0° C. overnight. Na₂SO₃ (7.5 g) was added. After 1 h at room temperature, the mixture was extracted with EtOAc (3×). The combined organic layers were washed with brine, dried over Na₂SO₄, filtered, and concentrated in vacuo. Purification by flash chromatography gave the (R)-diol 18.

¹H NMR (500 MHz, CDCl₃) δ 7.30 (overlapping signals, 2H), 7.12 (d, J=7.1 Hz, 1H), 3.82 (d, J=11.2 Hz), 3.66 (d, J=11.2 Hz, 1H), 2.59 (s, 1H), 2.40 (s, 3H), 1.55 (s, 3H).

Step 2. Preparation of Chiral OZD Precursor 21

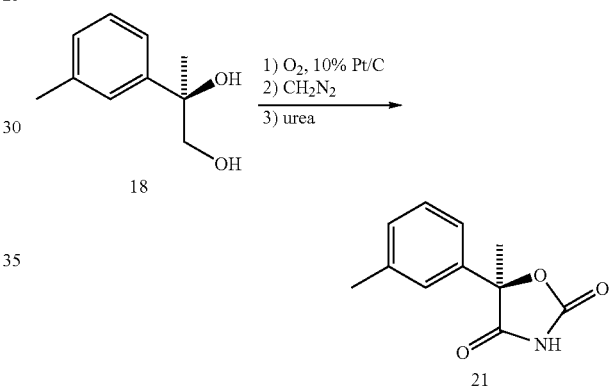

To a solution of the diol 18 (0.7 g) in water (50 mL) were added NaHCO₃ (0.4 g) and 10% Pt/C (0.7 g). Air was bubbled through the reaction mixture via a gas dispenser at 70° C. overnight. The reaction was cooled to room temperature, then filtered through Celite. The filtrate was acidified with aqueous H₂SO₄ (1.0 N) to pH 2, then extracted with EtOAc (3×). The combined organic layers were washed with brine, dried over Na₂SO₄, filtered, and concentrated in vacuo to give the acid.

To a solution of the above obtained acid (0.66 g) in ether (15 mL) was added a solution of CH₂N₂ in ether until the yellow color persisted. The solvent was removed in vacuo to give the methyl ester.

To a solution of the above obtained methyl ester (700 mg) in ethanol (10 mL) were added urea (316 mg) and a solution of sodium ethoxide in ethanol (21 wt %, 2.25 mL). The reaction was refluxed overnight, cooled to room temperature, and then partitioned between 1.0N aqueous HCl and EtOAc. The organic layer was washed with brine, dried over Na₂SO₄, filtered, and concentrated in vacuo. Purification by flash chromatography gave the product.

¹H NMR (500 MHz, CDCl₃) δ 8.70 (s, broad, 1H), 7.4-7.2 (overlapping signals, 4H), 2.40 (s, 3H), 1.96 (s, 3H).

Step 3. Preparation of Intermediate 23

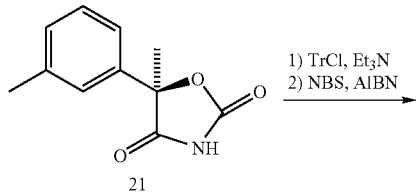

To a solution of the OZD 21 (0.60 g, 2.92 mmol)) in CH$_2$Cl$_2$ (10 mL) were added TrCl (1.25 g, 4.5 mmol) and Et$_3$N (0.63 mL, 4.5 mmol). After 3 h at room temperature, the reaction mixture was partitioned between water and ether. The organic layer was washed with water and brine, dried over Na$_2$SO$_4$, filtered, and concentrated in vacuo. Purification by flash chromatography gave the product.

To a solution of the above obtained trityl protected OZD (1.2 g, 2.68 mmol) in CCl$_4$ (30 mL) were added NBS (0.47 g, 2.68 mmol) and a catalytic amount of AIBN. The reaction was refluxed overnight, cooled to room temperature, filtered, and concentrated in vacuo. Purification by chromatography gave the benzyl bromide product 23.

$^1$H NMR (500 MHz, CDCl$_3$) δ 7.6-7.2 (overlapping signals, 19H), 4.52 (s, 2H), 1.77 (s, 3H).

Step 4. Preparation of Chiral OZD 25.

To a solution of indole 14, which is Compound 5 of Scheme 2 (90 mg, 0.25 mmol), in DMF (10 mL) at room temperature were added bromide 23 (130 mg, 0.25 mmol) and Cs$_2$CO$_3$ (170 mg, 0.52 mmol). The reaction was stirred for 5 h, and then was partitioned between water and diethyl ether. The organic layer was washed with brine, dried over Na$_2$SO$_4$, filtered, and concentrated in vacuo. Purification by flash chromatography gave the coupling product.

The above obtained product was dissolved in trifluoroacetic acid (3.5 mL). The reaction mixture was stirred at room temperature for 0.5 h, then evaporated to dryness in vacuo. The residue was purified by flash chromatography to give 25.

$^1$H NMR (500 MHz, CDCl$_3$) δ 7.90 (s, broad, 1H), 7.77 (d, J=8.5 Hz, 2H), 7.55 (d, J=7.8 Hz), 7.49 (d, J=8.4 Hz, 2H), 7.42 (s, 1H), 7.39 (overlapping signals, 2H), 7.12 (s, 1H), 7.02 (d, J=8.8 Hz, 1H), 6.88 (d, J=7.8 Hz, 1H), 5.42 (s, 2H), 2.55 (s, 1H), 1.92 (s, 3H).

Example 4

See Scheme 8

Step 1. Preparation of Intermediate 27

Cyclic diketal 26 was prepared based on literature procedure. To a solution of 26 (3 g, 16.85 mmol) in THF (30 mL) at −78° C. was added LiHMDS (1.0 M in THF, 17.7 mL). After 10 min, the enolate solution thus formed was transferred via a canula to a solution of MeI (3.15 mL, 50.6 mmol) in THF (50 mL) at −78° C. The reaction was allowed to slowly warm to 0° C. over 3 h, quenched with saturated aqueous NH$_4$Cl, and then partitioned between water and diethyl ether. The organic layer was washed with brine, dried over Na₂SO₄, filtered, and concentrated in vacuo. Purification by flash chromatography gave the methylated product.

To a solution of the above obtained product (1.0 g, 5.21 mmol) in THF (30 mL) at −78° C. was added LiHMDS (1.0 M in THF, 5.7 mL). After 10 min, the benzyl bromide (2.0 g) was added. The reaction was allowed to slowly warm to 0° C. over 3 h, quenched with saturated aqueous NH₄Cl, and then partitioned between water and diethyl ether. The organic layer was washed with brine, dried over Na₂SO₄, filtered, and concentrated in vacuo. Purification by flash chromatography gave the product 27.

¹H NMR (500 MHz, CDCl₃) δ 7.3-7.2 (overlapping signals, 4H), 4.47 (s, 2H), 3.41 (s, 3H), 3.28 (s+s+d, 7H), 2.89 (d, J=13.0 Hz, 1H), 1.52 (s, 3H), 1.43 (s, 3H), 1.40 (s, 3H).

Step 2. Preparation of Intermediate 29

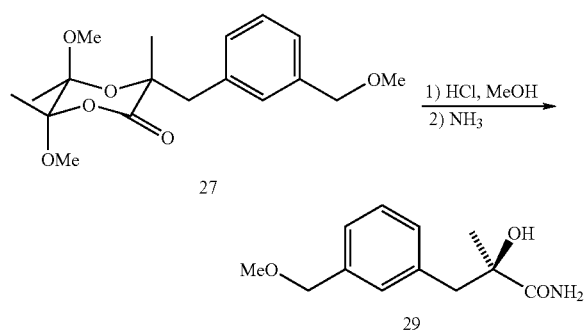

To a solution of 27 (1.0 g) in MeOH (25 mL) was added TMSCl (2.5 mL). The reaction was refluxed overnight. After cooling to room temperature, the solvent was removed in vacuo to give the methyl ester.

The above obtained methyl ester (0.69 g) was dissolved in MeOH (20 mL). A stream of ammonia was bubbled through at 0° C. for 20 min. The reaction flask was sealed and allowed to warm to room temperature. After 72 h, the solvent was removed to give the amide 29.

¹H NMR (500 MHz, CDCl₃) δ 7.34 (t, J=7.6 Hz, 1H), 7.29 (d, J=7.6 Hz, 1H), 7.24 (s, 1H), 7.20 (d, J=7.5 Hz, 1H), 6.56 (s, broad, 1H), 5.44 (s, broad, 1H), 4.47 (s, 2H), 3.43 (s, 3H), 3.33 (d, J=13.5 Hz, 1H), 2.88 (d, J=13.5 Hz, 1H), 1.50 (s, 3H).

Step 3. Preparation of Intermediate 32.

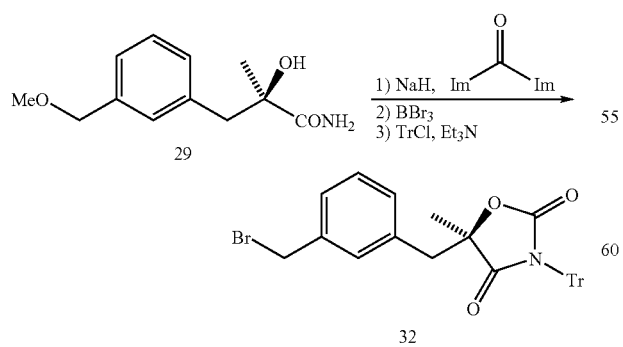

To a solution of amide 29 (78 mg) in dimethyl carbonate (8 mL) were added NaH (25 mg) and carbonyl diimidazole (160 mg). The reaction mixture was stirred at 40° C. overnight, and then was partitioned between Et2O and 1.0 N aqueous HCl. The organic layer was washed with brine, dried over Na₂SO₄, filtered, and concentrated in vacuo to give the OZD product.

To a solution of the above obtained product in CH₂Cl₂ (5 mL) at −78° C. was added BBr₃ (0.5 mL). The reaction was allowed to warm to room temperature. After 45 min, the reaction was quenched by water, extracted with EtOAc. The organic layer was washed with water and brine, dried over Na₂SO₄, filtered, and concentrated in vacuo to give the benzyl bromide product.

To a solution of the above obtained product (80 mg0) in CH₂Cl₂ (3 mL) were added TrCl (75 mg) and Et₃N (38 μL). After 45 min at room temperature, the reaction mixture was partitioned between water and ether. The organic layer was washed with water and brine, dried over Na₂SO₄, filtered, and concentrated in vacuo. Purification by flash chromatography gave the intermediate 32.

¹H NMR (500 MHz, CDCl₃) δ 7.52 (d, J=7.5 Hz, 1H), 7.47 (t, J=7.5 Hz, 1H), 7.41 (s, 1H), 7.31 (d, J=7.5 Hz, 1H), 7.20 (m, 9H), 7.01 (m, 6H), 4.57 (d, J=10.5 Hz, 1H), 4.55 (d, J=10.6 Hz, 1H), 3.17 (s, 2H), 1.50 (s, 3H).

Step 4. Preparation of Chiral OZD 33.

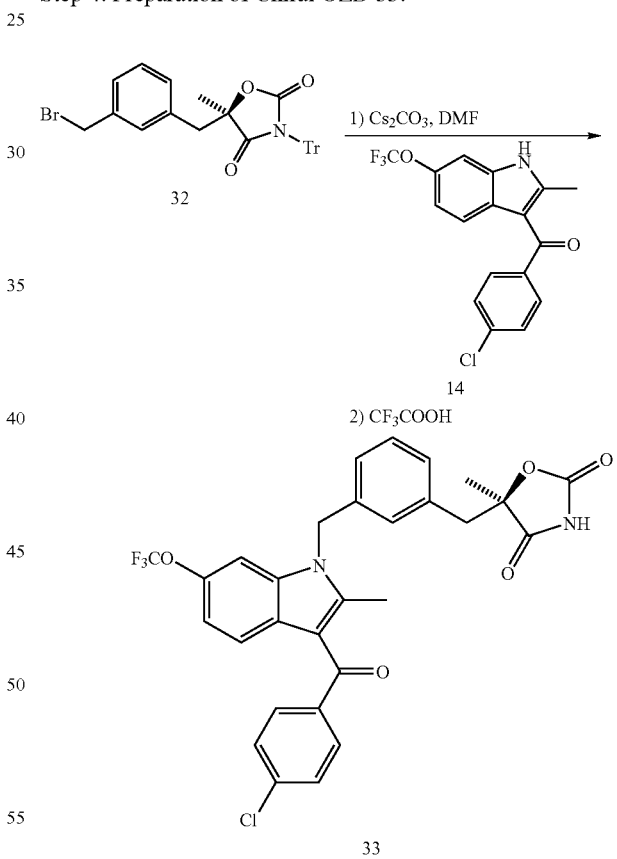

To a solution of indole 14, which is Compound 5 of Scheme 2 (19 mg), in DMF (1.0 mL) at room temperature were added bromide 32 (29 mg) and Cs₂CO₃ (35 mg). The reaction was stirred for 5 h, and then was partitioned between water and diethyl ether. The organic layer was washed with brine, dried over Na₂SO₄, filtered, and concentrated in vacuo. Purification by preparative TLC plates gave the coupling product.

The above obtained product was dissolved in trifluoroacetic acid (2 mL). The reaction mixture was stirred at room temperature for 0.5 h, then evaporated to dryness in vacuo. The residue was purified by flash chromatography to give 33.

¹H NMR (500 MHz, CDCl₃) δ 8.60 (s, broad, 1H), 7.84 (d, J=8.4 Hz, 2H), 7.50 (d, J=8.5 Hz), 7.33 (t, J=7.6 Hz, 1H), 7.29 (d, J=8.5 Hz, 1H), 7.19 (s, 1H), 7.16 (d+d, 2H), 7.03 (d, J=7.7 Hz, 1H), 6.46 (s, 1H), 5.48 (d, J=16.9 Hz, 1H), 5.25 (d, J=16.9 Hz, 1H), 3.10 (d, J=14.2 Hz, 1H), 2.98 (d, J=14.2 Hz, 1H), 2.42 (s, 3H), 1.60 (s, 3H).

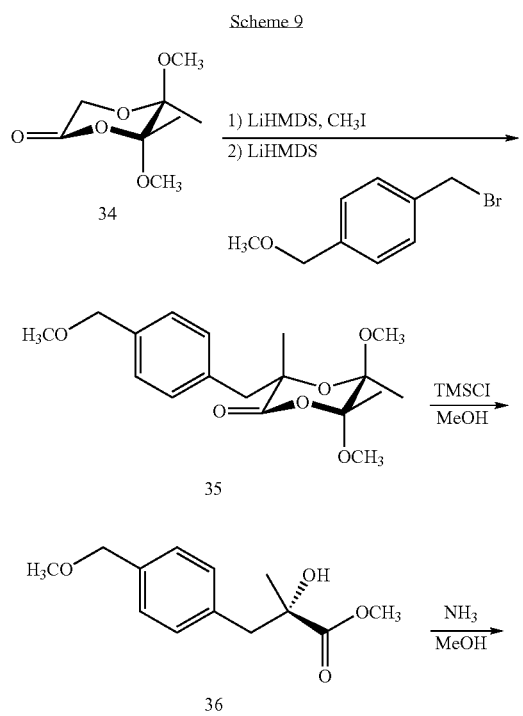

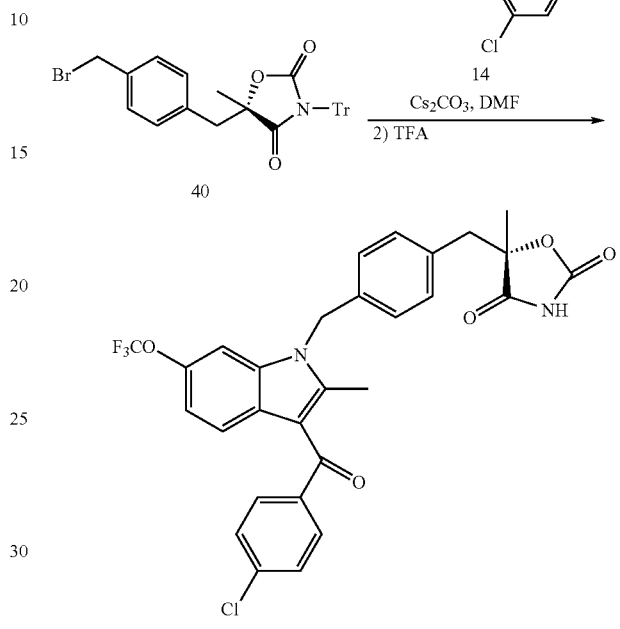

Example 5

See Scheme 9

Step 1. Preparation of Intermediate 35

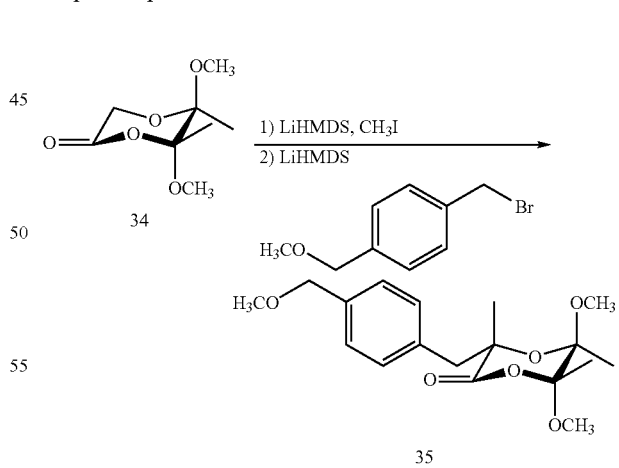

Cyclic diketal 34 was prepared according to literature procedures. To a solution of 34 (1.77 g, 9.3 mmol) in THF (20 mL) at −78° C., was added a 1 M solution of lithium bis(trimethylsilyl)amide (9.3 mL). Ten minutes later, methyl iodide (0.58 mL, 9.3 mmol) was added in a single portion. The mixture was allowed to slowly warm to 0° C. over 2 h. Then it was cooled to −78° C. and the second portion of lithium bis(trimethylsilyl)amide (9.3 mL) was added, followed by a solution of p-methoxymethyl benzyl bromide (2.0 g, 9.3 mmol) in THF (5 mL). The mixture was again allowed to warm slowly to 0° C. over 2 h and quenched with saturated aqueous ammonium chloride. The mixture was extracted with diethyl ether, and the organic layer was washed with brine, dried over magnesium sulfate and concentrated in vacuo. Purification by silica gel chromatography afforded product 35.

$^1$H NMR (500 MHz, CDCl$_3$) δ 7.25-7.31 (overlapping signals, 4H), 4.48 (s, 2H), 3.44 (s, 3H), 3.30 (s+s+d, 7H), 2.89 (d, 1H, J=13.0 Hz), 1.54 (s, 3H), 1.43 (s, 3H), 1.41 (s, 3H).

Step 2. Preparation of Intermediate 37

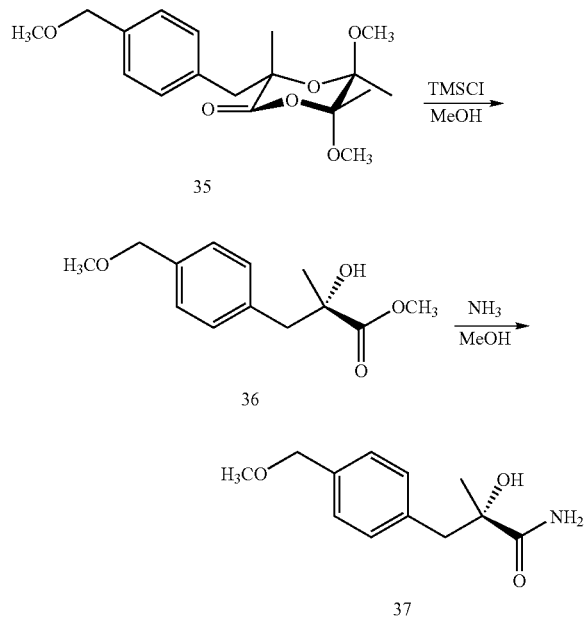

To a solution of 35 (1.65 g) in methyl alcohol (40 mL) was added chlorotrimethylsilane (3 mL). The mixture was refluxed for 18 h. After cooling to room temperature, volatiles were removed in vacuo to give 36. The methyl ester 36 was then dissolved in methyl alcohol (20 mL). A stream of ammonia was bubbled through at 0° C. for 20 minutes. The reaction flask was sealed and kept at room temperature for 72 h. Volatiles were removed in vacuo to give amide 37.

$^1$H NMR (500 MHz, CDCl$_3$) δ 7.33 (d, 2H, J=7.5 Hz), 7.25 (d, 2H, J=7.5 Hz), 6.57 (s, br, 1H), 5.40 (s, br, 1H), 4.42 (s, 2H), 3.42 (s, 3H), 3.33 (d, 1H, J=13.5 Hz), 2.82 (d, 1H, J=13.5 Hz), 1.51 (s, 3H).

Step 3. Preparation of Intermediate 40

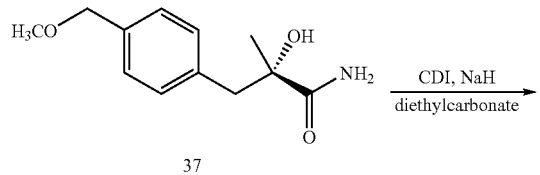

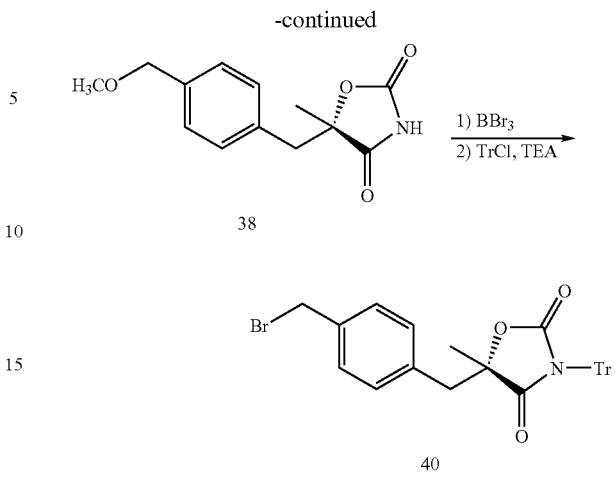

To a solution of amide 37 (from 4.87 mmol of 35) in diethylcarbonate (10 mL) was added carbonyldiimidazole (2.4 g, 14.6 mmol) and sodium hydride (0.6 g, 24.3 mmol). The reaction mixture was stirred at 50° C. for 15 h. It was quenched with ice-water, and neutralized with a sufficient amount of dilute hydrochloric acid. After partitioning between diethyl ether and water, the organic phase was washed with brine, dried over magnesium sulfate and evaporated to give intermediate 38. This OZD intermediate was treated with 1 M boron tribromide (10 mL) in dichloromethane at 0° C. and stirred at room temperature for 15 h. The reaction was quenched with ice-water, and the mixture was extracted with ethyl acetate. The organic phase was washed sequentially with water and brine, dried over magnesium sulfate and evaporated in vacuo. The residue was dissolved in dichloromethane, and to this solution was added trityl chloride (1.35 g, 4.87 mmol) and triethylamine (0.68 mL, 4.87 mmol). After 1 h at room temperature, the reaction mixture was partitioned between diethyl ether and water. The ether phase was washed with brine, dried over sodium sulfate and concentrated to a solid residue. Purification by silica gel chromatography gave intermediate 40.

$^1$H NMR (500 MHz, CDCl$_3$) δ7.51 (d, 2H, J=7.5 Hz), 7.35 (d, 2H, J=7.5 Hz), 7.19 (m, 9H), 7.02 (m, 6H), 4.58 (s, 2H), 3.08 (s, 2H), 1.43 (s, 3H).

Step 4. Preparation of Chiral OZD 41

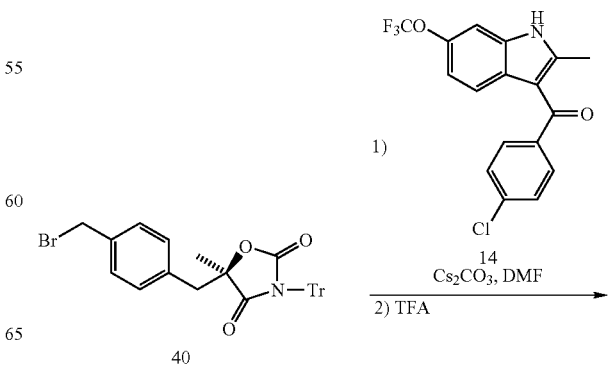

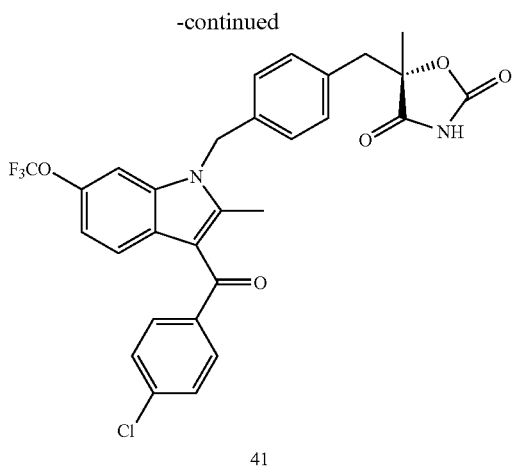

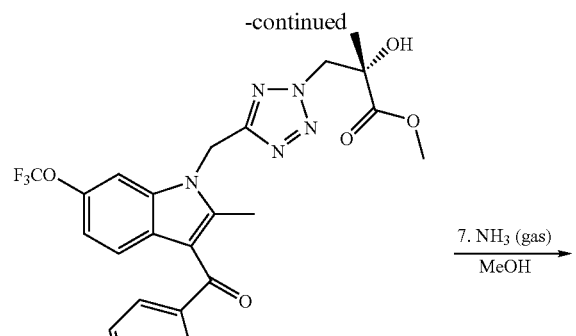

Compound 40 (0.31 g, 0.57 mmol) was mixed with indole intermediate 14 (0.20 g, 0.57 mmol), which is Compound 5 of Scheme 2, and cesium carbonate (0.56 g, 1.7 mmol) in dimethylformamide (5 mL). The reaction was stirred at room temperature for 2 h. It was partitioned between diethyl ether and water. The organic phase was washed with water and brine, dried over magnesium sulfate, and evaporated in vacuo. The crude trityl protected OZD was treated with trifluoroacetic acid (5 mL) at room temperature for 1 h. After evaporating off the volatiles, the residue was purified by silica gel chromatography to give 41.

$^1$H NMR (500 MHz, CDCl$_3$) δ 7.75 (d, 2H, J=8.5 Hz), 7.48 (d, 2H, J=8.5 Hz), 7.39 (s, 1H), 7.33 (d, 1H, J=9.0 Hz), 7.22 (d, 2H, J=8.0 Hz), 7.12 (s, 1H), 7.02 (s, 1H), 7.01 (d, 2H, J=8.5 Hz), 5.36 (s, 2H), 3.15 (q, 2H, J=14.5 Hz), 2.54 (s, 3H), 1.67 (s, 3H).

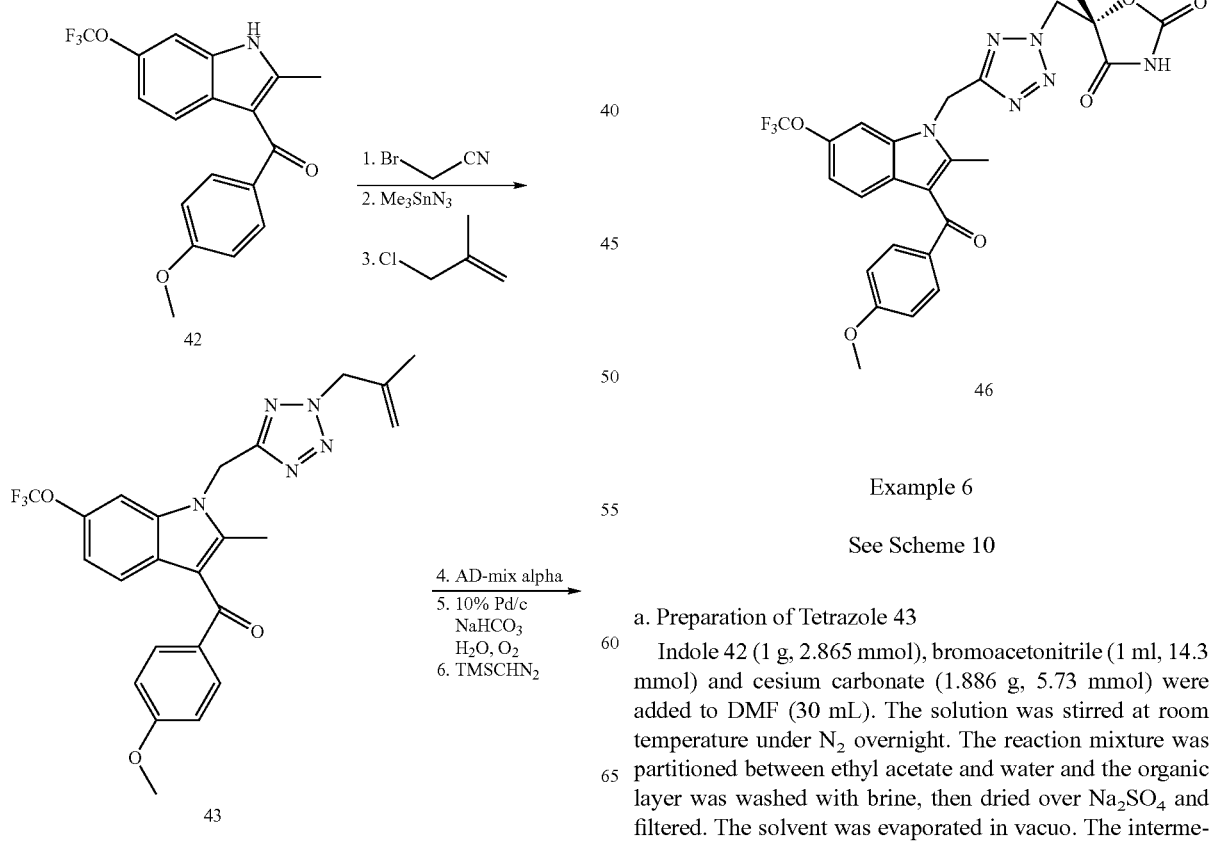

Example 6

See Scheme 10 a. Preparation of Tetrazole 43

Indole 42 (1 g, 2.865 mmol), bromoacetonitrile (1 ml, 14.3 mmol) and cesium carbonate (1.886 g, 5.73 mmol) were added to DMF (30 mL). The solution was stirred at room temperature under N$_2$ overnight. The reaction mixture was partitioned between ethyl acetate and water and the organic layer was washed with brine, then dried over Na$_2$SO$_4$ and filtered. The solvent was evaporated in vacuo. The intermediate nitrile thus prepared was purified by column chromatography on silical gel using gradient elution (5% to 60% ethyl acetate in hexane).

The resulting nitrile (900 mg, 2.32 mmol) was dissolved in dry THF (23.2 mL). Azidotrimethyltin (1.43 g, 6.96 mmol) was added to this solution. The reaction mixture was heated to reflux under $N_2$ overnight. The solvent was then evaporated on vacuo. The tetrazole thus prepared was purified by column chromatography on silica gel using gradient elution (5% to 100% ethyl acetate in hexane).

The resulting tetrazole (500 mg, 1.16 mmol), 3-chloro-2-methyl propene (0.23 mL, 2.22 mmol), and cesium carbonate (567 mg, 1.174 mmol) were dissolved in DMF (11.6 mL) and stirred at 50° C. under $N_2$ overnight. The reaction mixture was partitioned between ethyl acetate and water, the organic layer was washed with brine and then dried over $Na_2SO_4$ and filtered. The solvent was evaporated in vacuo. Pure tetrazole 43 was obtained following column chromatography on silica gel using gradient elution (5% to 50% ethyl acetate in hexane).

Selected Signals: $^1$H NMR (CDCl$_3$) δ 7.82 (d, 2H, J=8.6 Hz), 7.44 (s, 1H), 7.42 (d, 1H, J=8.7 Hz), 7.02 (d, 1H, J=8.9 Hz), 6.99 (d, 2H, J=8.7 Hz), 5.6 (s, 2H), 5.15 (s, 2H,), 5.12 (s, 1H), 4.98 (s, 1H), 3.93 (s, 3H,), 2.76 (s, 3H), 1.73 (s, 3H).

b. Preparation of Methyl Ester 44

To a suspension of tetrazole 43 (480 mg, 0.989 mmol) in 1:1 tBuOH/H$_2$O (10 mL) at 0° C. was added AD-mix alpha (1.4 g). The reaction mixture was warmed gradually to room temperature and stirred for 2 days. The solvent was evaporated in vacuo. The reaction mixture was partitioned between ethyl ether and water. The organic layer was washed with brine, then dried over $Na_2SO_4$ and filtered. The solvent was evaporated in vacuo. The resultant diol was purified by column chromatography on silica gel using gradient elution (5% to 100% ethyl acetate in hexane).

To a suspension of pure diol (370 mg) was added 10% Pd/C (370 mg) and NaHCO$_3$ (212.75 mg) in 92.5 mL H$_2$O and air was bubbled thru a gas dispensor at 70° C. overnight. The reaction mixture was cooled to room temperature, filtered through a bed of celite and washed with water. The filtered solution was acidified with 1N H$_2$SO$_4$ to pH2 and extracted with ethyl acetate 3 times. The combined organic layers were washed with brine, dried over Na$_2$SO$_4$ and filtered. The solvent was evaporated in vacuo.

To a solution of the resulting carboxylic acid (210 mg, 0.394 mmol) in 3:1 benzene/MeOH (2.8 mL) was added 2M (trimethylsilyl)diazomethane/THF (0.273 mL). The reaction mixture was stirred at room temperature for 30 min. The solvent was evaporated on vacuo to obtain desired methyl ester 44.

Selected Signals: $^1$H NMR (CDCl$_3$) δ 7.82 (d, 2H, J=8.9 Hz), 7.43 (d, 1H, J=8.7 Hz), 7.40 (s, 1H,), 7.03 (d, 1H, J=8.7 Hz), 6.99 (d, 2H, J=8.7 Hz), 5.59 (d, 2H, J=1.1), 4.87 (dd, 2H, J=30.1 Hz, 13.8 Hz), 3.94 (s, 3H), 3.74 (s, 3H), 2.72 (s, 3H,), 1.59 (s, 3H).

c. Preparation of Chiral OZD 46

Methyl ester 44 (100 mg) was dissolved in MeOH in a tube with a threaded top. NH$_3$ gas was bubbled through the solution at 0° C. for 30 min. Then tube then was sealed and reaction mixture was aged at room temperature without stirring for 24 hours. The volatiles were removed in vacuo then dried further on the high vacuum pump overnight.

To a solution of the resulting amide 45 (100 mg, 0.188 mmol) in ethyl carbonate (2.85 mL) was added NaH (23 mg, 0.95 mmol, 60% dispersion in mineral oil), followed by addition of 1,1'-carbonyldiimidazole (92.5 mg, 0.564 mmol). The reaction mixture was stirred at 50° C. for 6 hours and then partitioned between ethyl acetate and water. The combined organic layer was washed with brine, dried over Na$_2$SO$_4$ and filtered. The solvent was evaporated in vacuo. Following purification by column chromatography on silica gel using gradient elution (5% to 100% ethyl acetate in hexane) to give desired OZD 46.

Selected Signals: $^1$H NMR (CDCl$_3$) δ 7.93 (d, 2H, J=8.7 Hz), 7.3 (d, 1H, J=8.4 Hz), 7.3 (s, 1H,), 7.01 (m, 3H), 5.56 (d, 2H, J=6.7 Hz), 4.94 (dd, 2H, J=53.3 Hz, 14.6 Hz), 3.95 (s, 3H), 3.65 (s, 3H), 1.69 (s, 3H). MS: m/z=559.0 (M+1)

What is claimed is:
1. A compound of formula I:

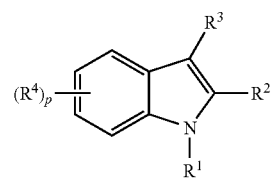

or a pharmaceutically acceptable salt thereof, wherein:
$R^1$ is selected from
  (a) —X-Aryl-Y-Z, and
  (b) —X-Heteroaryl-Y-Z,
wherein Aryl and Heteroaryl are optionally substituted with 1-3 groups independently selected from A, where A can be on any position of Heteroaryl when $R^1$ is —X-Heteroaryl-Y-Z;
Aryl is phenyl or naphthyl;
Heteroaryl is a monocyclic or fused bicyclic aromatic ring containing 1-4 heteroatoms independently selected from N, O and S, including —S(O)— and —S(O)$_2$—, wherein each ring contains 5 to 6 atoms;
X and Y are independently selected from the group consisting of a bond and —CR$^5$R$^6$—;
Z is

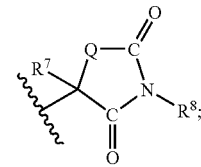

Q is selected from the group consisting of S and O;
A is selected from the group consisting of $C_1$-$C_4$ alkyl, $C_2$-$C_4$ alkenyl, —OC$_1$-$C_4$ alkyl, and halogen, wherein alkyl, alkenyl, and —Oalkyl are each optionally substituted with 1-5 halogens;
$R^2$ is $C_1$-$C_4$ alkyl, which is optionally substituted with 1-5 halogens;
$R^3$ is selected from the group consisting of
  (a) Benzisoxazolyl,
  (b) Aryl,
  (c) —C(=O)Aryl,
  (d) —OAryl, and
  (e) —S(O)$_n$Aryl,
wherein $R^3$ is optionally substituted with 1-3 substituent groups independently selected from halogen, $C_1$-$C_3$ alkyl, and —OC$_1$-$C_3$ alkyl, wherein $C_1$-$C_3$ alkyl and —OC$_1$-$C_3$ alkyl are optionally substituted with 1-5 halogens;
$R^4$, $R^5$, and $R^6$ are independently selected from the group consisting of hydrogen, halogen, $C_1$-$C_3$ alkyl, and —OC$_1$-C$_3$ alkyl, wherein C$_1$-C$_3$ alkyl and —OC$_1$-C$_3$ alkyl are optionally substituted with 1-5 halogens;

R$^7$ is selected from the group consisting of H, C$_1$-C$_3$ alkyl, and halogen, wherein C$_1$-C$_3$ alkyl is optionally substituted with 1-3 F;

R$^8$ is selected from the group consisting of H and CH$_3$;

n is an integer from 0 to 2; and p is an integer from 0 to 3.

2. The compound of claim 1, or a pharmaceutically acceptable salt thereof, wherein R$^8$ is H.

3. The compound of claim 1, or a pharmaceutically acceptable salt thereof, wherein R$^1$ is —X-phenyl-YZ, wherein phenyl is optionally substituted with 1-2 groups independently selected from A.

4. The compound of claim 1, or a pharmaceutically acceptable salt thereof, wherein X and Y are each independently selected from a bond and —CH$_2$—.

5. The compound of claim 1, or a pharmaceutically acceptable salt thereof, wherein A is selected from the group consisting of halogen, —CF$_3$, —OCF$_3$, —CH$_3$, and —OCH$_3$.

6. The compound of claim 1, or a pharmaceutically acceptable salt thereof, wherein R$^2$ is selected from C$_{1-3}$ alkyl and —CF$_3$.

7. The compound of claim 1, or a pharmaceutically acceptable salt thereof, wherein R$^2$ is —CH$_3$.

8. The compound of claim 1, or a pharmaceutically acceptable salt thereof, wherein R$^4$ is selected from the group consisting of —OCH$_3$, —OCF$_3$, —CH$_3$ and —CF$_3$; and p is 1.

9. The compound of claim 1, or a pharmaceutically acceptable salt thereof, wherein R$^3$ is selected from the group consisting of:

(a) 3-Benzisoxazolyl,
(b) Phenyl,
(c) —C(=O)Phenyl, and
(d) —OPhenyl, wherein R$^3$ is optionally substituted with 1-2 groups independently selected from halogen, —OCH$_3$, —OCF$_3$, CH$_3$, and CF$_3$.

10. The compound of claim 9, or a pharmaceutically acceptable salt thereof, wherein R$^1$ is —X-phenyl-YZ, wherein phenyl is optionally substituted with 1-2 groups independently selected from A;

X and Y are independently selected from a bond and —CH$_2$—;

A is selected from the group consisting of F, Cl, I, —CF$_3$, —OCF$_3$, —CH$_3$, and —OCH$_3$;

R$^2$ is —CH$_3$;

R$^4$ is selected from the group consisting of Cl, —CF$_3$, —OCF$_3$, —CH$_3$, and —OCH$_3$;

R$^7$ is selected from the group consisting of H, CH$_3$, and CF$_3$;

R$^8$ is H; and p is 1.

11. The compound of claim 10, or a pharmaceutically acceptable salt thereof, wherein Q is O, and X and Y are —CH$_2$—.

12. The compound of claim 10, or a pharmaceutically acceptable salt thereof, wherein Q is O, X is —CH$_2$—, and Y is a bond.

13. The compound of claim 1, or a pharmaceutically acceptable salt thereof, wherein R$^1$ is —X-Heteroaryl-YZ, wherein Heteroaryl is selected from the group consisting of pyridinyl, quinolyl, furyl, tetrazolyl, isoxazolyl, oxazolyl, azoxazolyl, pyrazolyl, and thiazolyl, wherein Heteroaryl is optionally substituted with 1-3 groups independently selected from A.

14. The compound of claim 1, selected from the group of compounds represented by the structures below, or a pharmaceutically acceptable salt thereof:

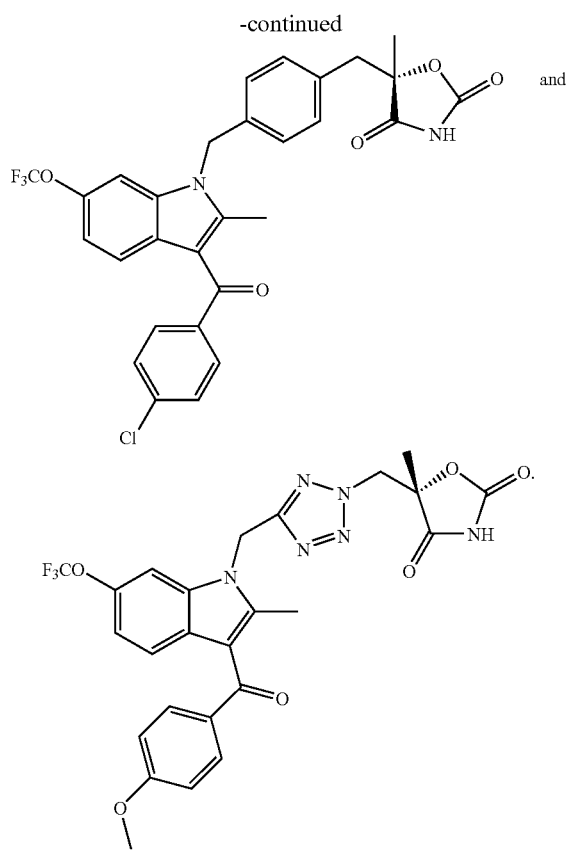
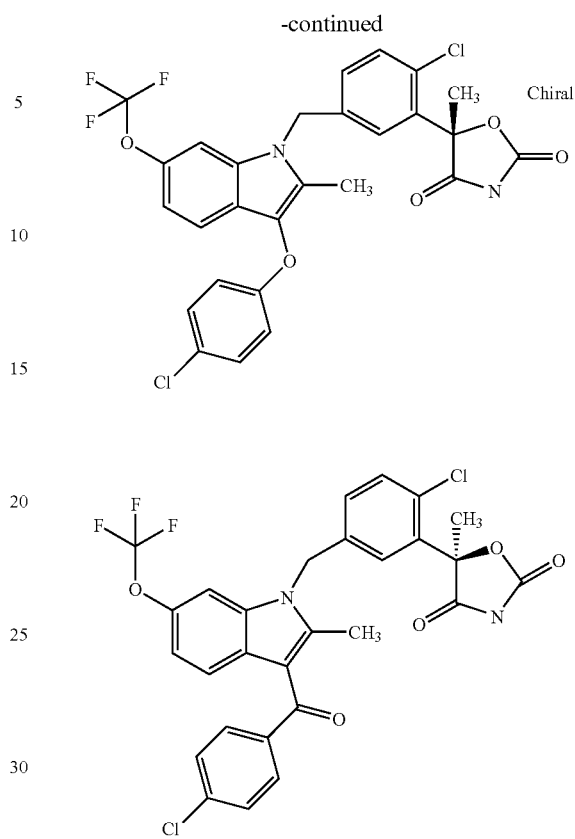
15. The compound of claim 1, selected from the group of compounds represented by the structures below, or a pharmaceutically acceptable salt thereof:
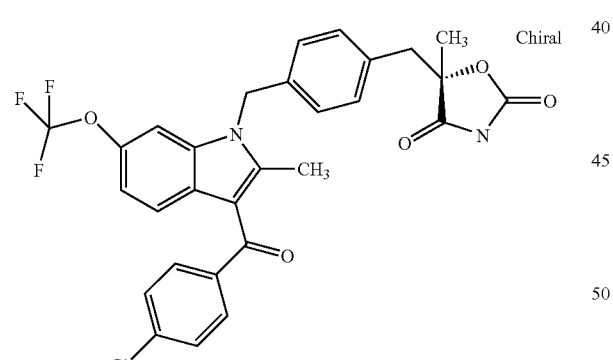
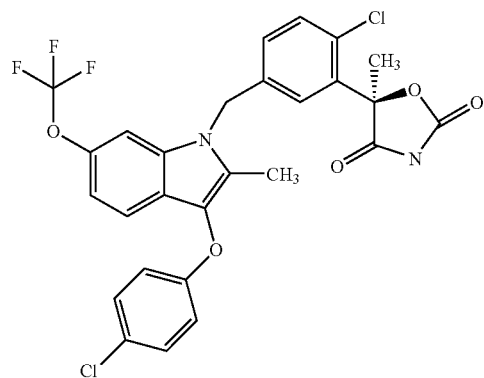
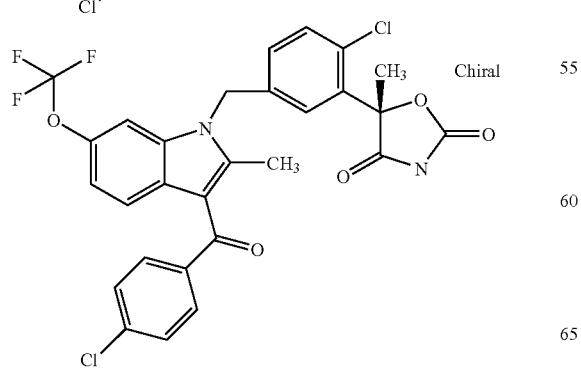
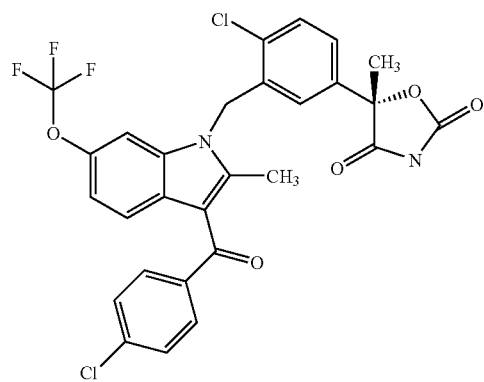

-continued
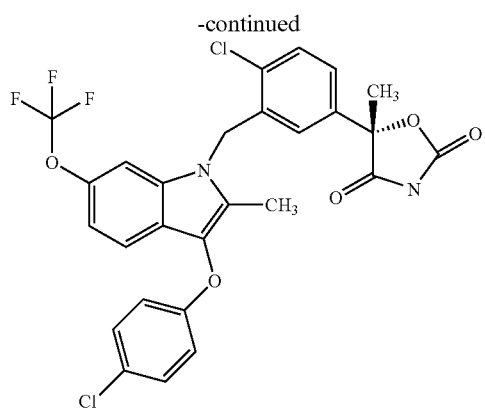
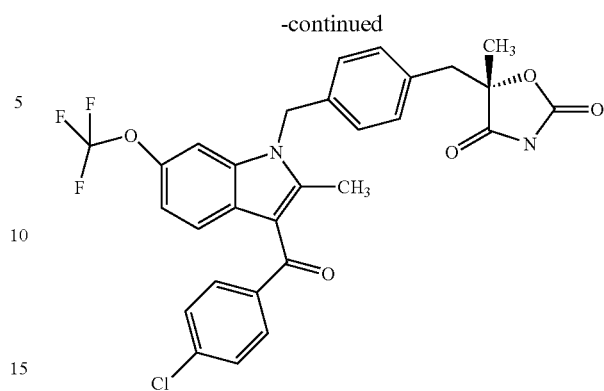
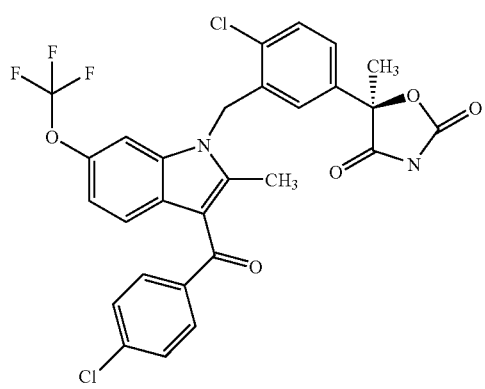
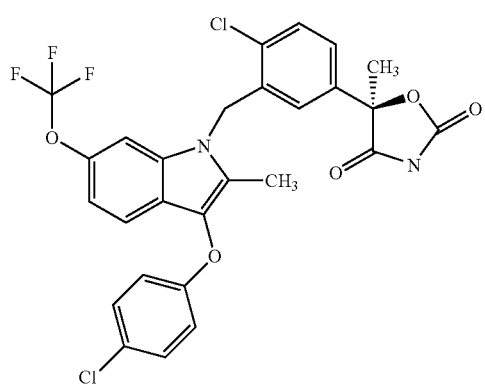
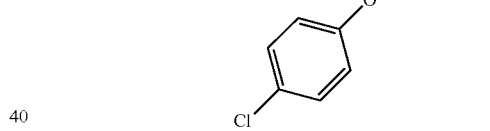
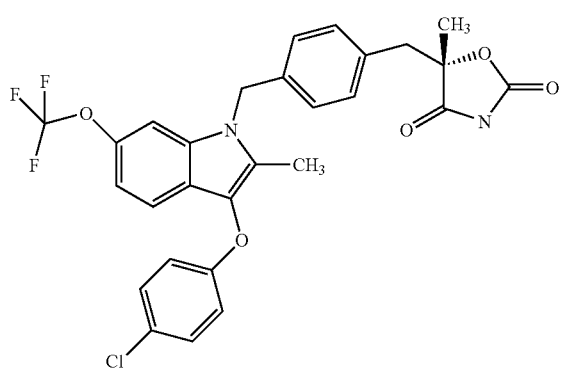
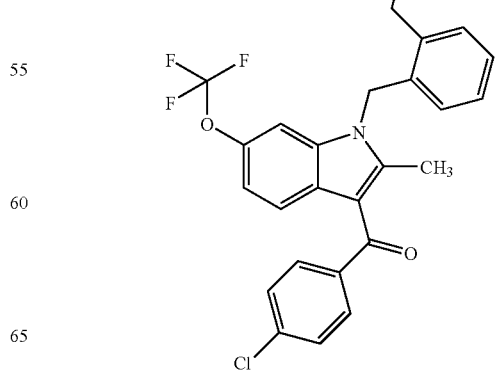

-continued

-continued
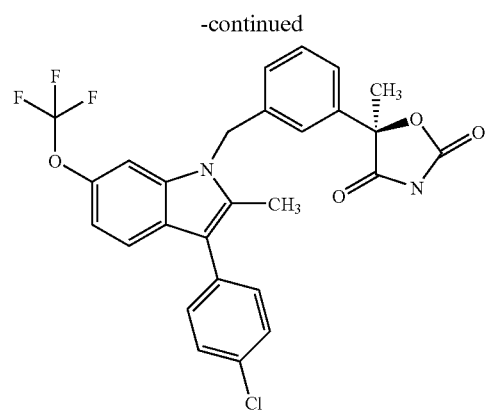
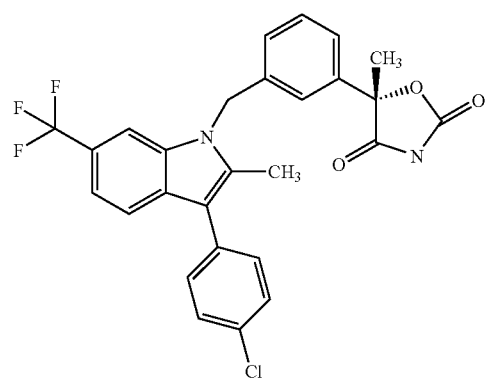
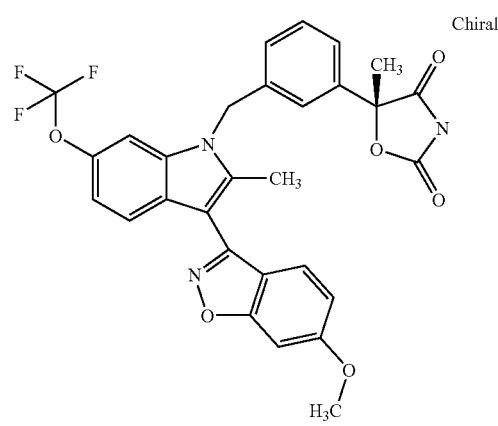
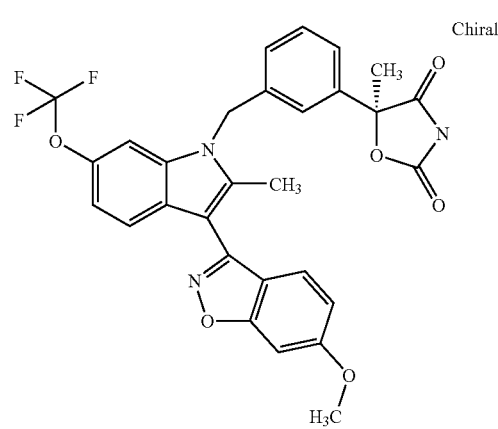
-continued
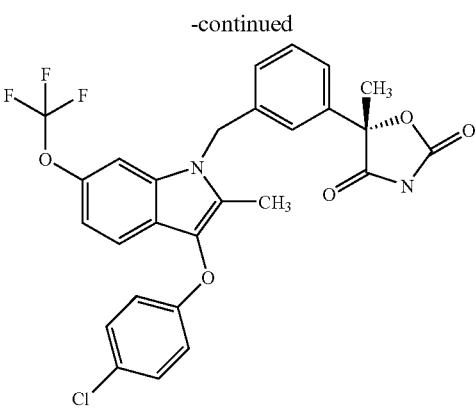
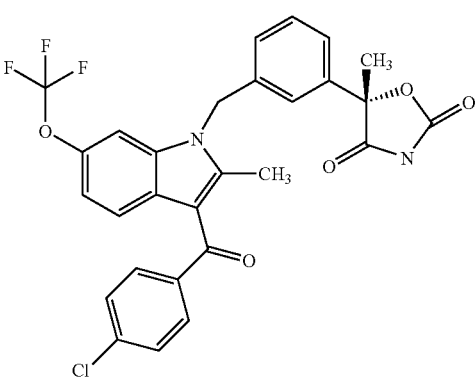
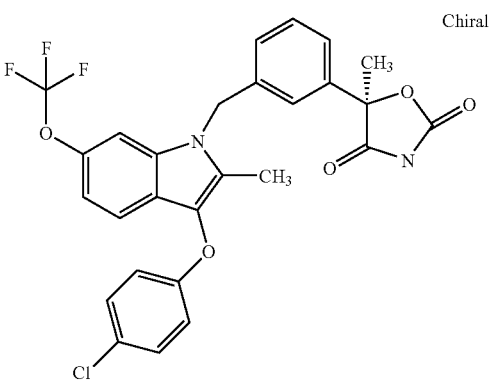
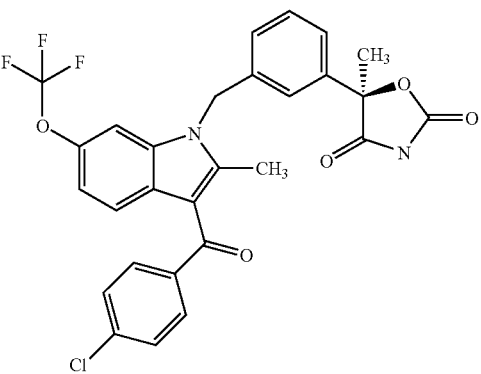

-continued

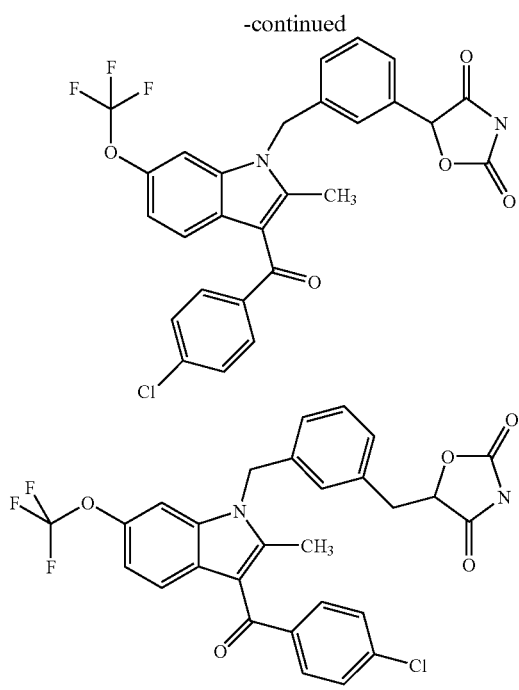

and

-continued

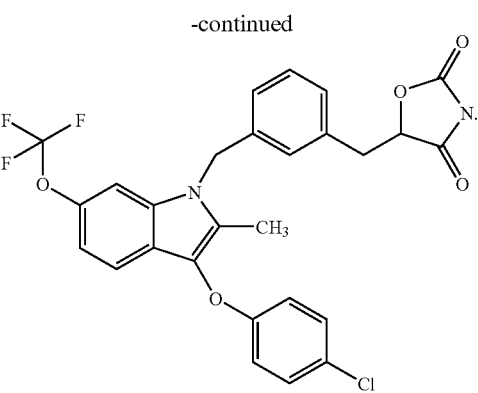

16. A pharmaceutical composition comprising a compound of claim 1, or a pharmaceutically acceptable salt thereof, and a pharmaceutically acceptable carrier.

17. A method for treating non-insulin dependent (Type 2) diabetes mellitus in a patient in need of such treatment which comprises administering to said patient a therapeutically effective amount of the compound of claim 1, or a pharmaceutically acceptable salt thereof.

* * * * *